United States Patent
Trumm et al.

(10) Patent No.: US 12,298,599 B2
(45) Date of Patent: May 13, 2025

(54) METHOD AND APPARATUS OPTIMIZING SPECTACLE LENSES FOR WEARERS OF IMPLANTED INTRAOCULAR LENSES

(71) Applicant: Rodenstock GmbH, Munich (DE)

(72) Inventors: Stephan Trumm, Munich (DE); Wolfgang Becken, Neuried (DE); Adam Muschielok, Munich (DE); Anne Seidemann, Munich (DE); Helmut Altheimer, Baisweil-Lauchdorf (DE); Gregor Esser, Munich (DE)

(73) Assignee: Rodenstock GmbH, Munich (DE)

( * ) Notice: Subject to any disclaimer, the term of this patent is extended or adjusted under 35 U.S.C. 154(b) by 671 days.

(21) Appl. No.: 17/624,008

(22) PCT Filed: Jul. 1, 2020

(86) PCT No.: PCT/EP2020/068572
§ 371 (c)(1),
(2) Date: Dec. 30, 2021

(87) PCT Pub. No.: WO2021/001452
PCT Pub. Date: Jan. 7, 2021

(65) Prior Publication Data
US 2022/0365367 A1    Nov. 17, 2022

(30) Foreign Application Priority Data
Jul. 2, 2019  (DE) .................. 102019004654.4

(51) Int. Cl.
*A61B 3/00*    (2006.01)
*G02C 3/00*    (2006.01)
(Continued)

(52) U.S. Cl.
CPC ............ *G02C 7/027* (2013.01); *A61B 3/0025* (2013.01); *G02C 7/028* (2013.01); *G02C 2202/22* (2013.01)

(58) Field of Classification Search
CPC ...... A61B 3/0025; G02C 7/027; G02C 7/028; G02C 2202/22
(Continued)

(56) References Cited

U.S. PATENT DOCUMENTS

2004/0246440 A1    12/2004    Andino et al.
2009/0009717 A1    1/2009    Barrett et al.
(Continued)

FOREIGN PATENT DOCUMENTS

CN        1553783 A      12/2004
CN      102713728 A      10/2012
(Continued)

OTHER PUBLICATIONS

European Patent Office, PCT International Search Report issued for PCT/EP2020/068571, 4 pgs., date of mailing: Oct. 16, 2020.
(Continued)

*Primary Examiner* — Mahidere S Sahle
(74) *Attorney, Agent, or Firm* — Banner & Witcoff Ltd.

(57) ABSTRACT

Optimizing a spectacle lens for a wearer of implanted intraocular lenses. The method includes providing individual refraction data on the at least one eye of the spectacle wearer; defining an individual eye model in which at least a shape and/or power of a cornea, in particular a corneal front surface, of a model eye, a cornea-lens distance, parameters of the lens of the model eye, and a lens-retina distance are defined as parameters of the individual eye model. Here, defining the parameters of the individual eye model takes place on the basis of data on visual acuity correction of the at least one eye having the intraocular lens and further on the
(Continued)

basis of individual measurement values for the eye of the spectacle wearer and/or standard values and/or on the basis of the provided individual refraction data such that the model eye has the provided individual refraction data.

22 Claims, 2 Drawing Sheets

(51) Int. Cl.
  *G02C 7/00* (2006.01)
  *G02C 7/02* (2006.01)
(58) Field of Classification Search
  USPC .................... 351/159.01, 159.74, 159.76
  See application file for complete search history.

(56) References Cited

U.S. PATENT DOCUMENTS

| | | | |
|---|---|---|---|
| 2013/0176536 A1* | 7/2013 | Thompson | A61B 3/0025 |
| | | | 351/233 |
| 2015/0002810 A1 | 1/2015 | Altheimer et al. | |
| 2016/0302660 A1 | 10/2016 | Bühren et al. | |
| 2018/0153681 A1* | 6/2018 | Rosen | A61B 3/0025 |
| 2019/0164647 A1 | 5/2019 | Rosén | |
| 2020/0285071 A1* | 9/2020 | Trumm | G02C 7/028 |

FOREIGN PATENT DOCUMENTS

| | | |
|---|---|---|
| CN | 104771133 A | 7/2015 |
| CN | 105263394 A | 1/2016 |
| CN | 105765446 A | 7/2016 |
| CN | 109008941 A | 12/2018 |
| DE | 102013020706 A1 | 6/2015 |
| DE | 102017007975 A1 | 8/2018 |
| EP | 3355098 A1 | 8/2018 |
| JP | 2003144387 A | 5/2003 |
| JP | 2007313313 A | 12/2007 |
| JP | 2015506499 A | 3/2015 |
| WO | 02088830 A1 | 11/2002 |
| WO | 03022137 A2 | 3/2003 |
| WO | 2018138140 A2 | 8/2018 |
| WO | 2018220737 A1 | 12/2018 |

OTHER PUBLICATIONS

Mar. 6, 2024 (JP) Office Action—App. 2021-578027 (w/English Translation).
May 28, 2024 (CN) Office Action—App. 202080048732.1.
Sep. 18, 2024 (JP) Office Action—App. 2021-578049 (w/English Translation).
Mar. 11, 2025 (CN) Office Action—App. 202080048591.3.

* cited by examiner

METHOD AND APPARATUS OPTIMIZING SPECTACLE LENSES FOR WEARERS OF IMPLANTED INTRAOCULAR LENSES

TECHNICAL FIELD

The present invention relates to a method, a device, and a corresponding computer program product for determining relevant individual parameters of at least one eye of a spectacle wearer for the calculation or optimization of a spectacle lens for the at least one eye of the spectacle wearer, and to a corresponding method, a device, and a computer program product for the calculation (optimization) and manufacture of a spectacle lens with the help of a partially individual eye model. Here, the at least one eye of the spectacle wearer has an implanted intraocular lens (IOL). For example, instead of or in addition to the natural eye lens, an intraocular lens can have been implanted in the at least one eye during surgery. In other words, the spectacle wearer is a wearer of an implanted intraocular lens. Moreover, the present invention relates to a method, a device and a corresponding computer program product for the calculation (optimization) and manufacture of a spectacle lens for a wearer of an implanted intraocular lens, with the help of a partially individual eye model.

BACKGROUND

For the manufacture or optimization of spectacle lenses, in particular individual spectacle lenses, each spectacle lens is manufactured such that for each desired viewing direction or each desired object point the best possible correction of a refractive error of the respective eye of the spectacle wearer is achieved. In general, a spectacle lens is considered to be fully correcting for a given viewing direction if the values for sphere, cylinder and axis of the wavefront upon passing the vertex sphere conform to the values for sphere, cylinder and axis of the prescription for the eye having the vision disorder. In the refraction determination for an eye of a spectacle wearer, dioptric values (in particular sphere, cylinder, cylinder axis—i.e. in particular sphero-cylindrical deviations) for a far (usually infinite) distance and optionally (for multifocal lenses or progressive lenses) an addition or a complete near refraction for a near distance (e.g. according to DIN 58208) are determined. In the case of modern spectacle lenses, object distances deviating from the norm, which are used in the refraction determination, can also be specified. In this way, the prescription (in particular sphere, cylinder, cylinder axis, and optionally addition or near refraction) to be communicated to a lens manufacturer is stipulated. Knowledge of a special or individual anatomy of the respective eye or the refractive values of the eye having the vision disorder, which are actually present in the individual case, is not required here.

However, a full correction for all viewing directions at the same time is normally not possible. Therefore, the spectacle lenses are manufactured such that they cause a good correction of vision disorders of the eye and only small aberrations particularly in the main zones of use, especially in the central visual zones, while larger aberrations are permitted in peripheral zones.

In order to be able to manufacture a spectacle lens in this way, the spectacle lens surfaces or at least one of the spectacle lens surfaces is first calculated such that the desired distribution of the unavoidable aberrations is effected thereby. This calculation and optimization is usually performed by means of an iterative variation method by minimizing a target function. As a target function, particularly a function F having the following functional relationship to the spherical power S, the magnitude of the cylindrical power Z, and the axis of the cylinder Δ (also referred to as "SZA" combination) is taken into account and minimized:

$$F = \sum_{i=1}^{m} \left[ g_{i,S\Delta}(S_{\Delta,i} - S_{\Delta,i,target})^2 + g_{i,Z\Delta}(Z_{\Delta,i} - Z_{\Delta,i,target})^2 + \ldots \right]$$

In the target function F, at the evaluation points i of the spectacle lens, at least the actual refractive deficits of the spherical power $S_{\Delta,i}$ and the cylindrical power as well as target specifications for the refractive deficits of the spherical power $S_{\Delta,i,target}$ and the cylindrical power $Z_{\Delta,i,target}$ are taken into consideration.

It was found in DE 103 13 275 that it is advantageous to not indicate the target specifications as absolute values of the properties to be optimized, but as their deviation from the prescription, i.e. as the required local maladjustment. The advantage is that the target specifications are independent of the prescription ($Sph_V, Zyl_V, Axis_V, Pr_V, B_V$) and that the target specifications do not have to be changed for every individual prescription. Thus, as "actual" values of the properties to be optimized, not absolute values of these optical properties are taken into account in the target function, but the deviations from the prescription. This has the advantage that the target values can be specified independent of the prescription and do not have to be changed for every individual prescription.

The respective refractive deficits at the respective evaluation points are preferably taken into consideration with weighting factors $g_{i,S\Delta}$ and $g_{i,z\Delta}$. Here, the target specifications for the refractive deficits of the spherical power $S_{\Delta,i,target}$ and/or the cylindrical power $Z_{\Delta,i,target}$, particularly together with the weighting factors $g_{i,S\Delta}$ and $g_{i,z\Delta}$, form the so-called spectacle lens design. In addition, particularly further residues, especially further parameters to be optimized, such as coma and/or spherical aberration and/or prism and/or magnification and/or anamorphic distortion, etc., can be taken into consideration, which is particularly implied by the expression "+ . . . " in the above-mentioned formula for the target function F.

In some cases, consideration not only of aberrations up to the second order (sphere, magnitude of the astigmatism, and cylinder axis) but also of higher order (e.g. coma, trefoil, spherical aberration) may in some cases contribute to a clear improvement particularly of an individual adaptation of a spectacle lens.

It is known from the prior art to determine the shape of a wavefront for optical elements and particularly spectacle lenses that are delimited by at least two refractive boundary surfaces. For example, this can be done by means of a numerical calculation of a sufficient number of neighboring rays, along with a subsequent fit of the wavefront data by Zernike polynomials. Another approach is based on local wavefront tracing in the refraction (cf. WO 2008/089999 A1). Here, only one single ray (the main ray) per visual point is calculated, accompanied by the derivatives of the vertex depths of the wavefront according to the transversal coordinates (perpendicular to the main ray). These derivatives can be formed up to a specific order, wherein the second derivatives describe the local curvature properties of the wavefront (such as refractive power, astigmatism), and the higher derivatives are related to the higher-order aberrations.

In the tracing of light through a spectacle lens, the local derivatives of the wavefront are calculated at a suitable position in the beam path in order to compare them with desired values obtained from the refraction of the spectacle lens wearer. As the position at which the wavefronts are evaluated, usually the vertex sphere or e.g. the principal plane of the eye for the corresponding direction of sight is considered. In this respect, it is assumed that a spherical wavefront emanates from the object point and propagates up to the first spectacle lens surface. There, the wavefront is refracted and subsequently propagates to the second spectacle lens surface, where it is refracted again. The last propagation takes place from the second boundary surface to the vertex sphere (or the principal plane of the eye), where the wavefront is compared with the predetermined values for the correction of the refraction of the eye of the spectacle wearer.

To make this comparison on the basis of the determined refraction data on the respective eye, an established model of the eye having the vision disorder, in which a base eye having normal vision is overlaid with a vision disorder (refractive deficit), is assumed for the evaluation of the wavefront at the vertex sphere. This has proven particularly successful as further knowledge of the anatomy or optics of the respective eye (e.g. distribution of the refractive powers, eye length, length ametropia and/or refractive power ametropia) is not required. A detailed description of this model of spectacle lens and refractive deficit can be found e.g. in Dr. Roland Enders "Die Optik des Auges und der Sehhilfen", Optische Fachveröffentlichung GmbH, Heidelberg, 1995, pages 25 ff. und in Diepes, Blendowske "Optik und Technik der Brille", Optische Fachveröffentlichung GmbH, Heidelberg, 2002, pages 47 ff. As a tried and tested model, in particular the described correction model according to REINER is used.

Here, the refractive deficit is considered to be the lack or excess of refractive power of the optical system of the eye having the vision disorder compared with an equally long eye having normal vision (residual eye). The refractive power of the refractive deficit is in particular approximately equal to the distance point refraction with negative sign. For a full correction of the vision disorder, the spectacle lens and the refractive deficit together from a telescopic system (afocal system). The residual eye (eye having the vision disorder without added refractive deficit) is considered to have normal vision. Thus, a spectacle lens is said to be fully correcting for distance if its image-side focal point coincides with the distance point of the eye having the vision disorder and thus also with the object-side focal point of the refractive deficit.

Document DE 10 2017 007 975 A1 or WO 2018/138140 A2, to which reference is expressly made herein or the content of which is fully included in the present description, describes a method and a device that allow improving the calculation or optimization of a spectacle lens, the spectacle lens being adapted very effectively to the individual requirements of the spectacle wearer with simple measurements of individual, optical and eye-anatomical data.

Patients with implanted intraocular lenses (IOL), i.e. patients who have undergone cataract surgery (e.g. as a result of cataract), are currently only provided with commercially available spectacle lenses, which are also used for patients with natural eye lenses. Thus, there are currently no specially adapted lenses for patients with IOLs. This means that the specifics of implanted IOLs cannot be taken into account, although the properties of implanted lenses differ significantly from those of natural lenses. For example, IOLs have a different spherical power for at least partially compensating for a corneal or length ametropia and/or a different cylindrical power for at least partially compensating for a corneal astigmatism or for at least partially cancelling out a lens astigmatism. In the case of conventionally optimized spectacle lenses, model-based properties are assumed for the eye lens, so that possibly the eye model used for the optimization in these cases no longer corresponds to the actual structure of the eye with an IOL, e.g. if a length ametropia is at least partially compensated for by the IOL due to the power (mean sphere) of the IOL.

SUMMARY

It is the object of the present invention to improve the calculation or optimization of a spectacle lens, preferably a progressive spectacle lens. In particular, it can be an object to provide patients with specially designed spectacle lenses after cataract surgery. In particular, it can be an object to improve the calculation or optimization of a spectacle lens, preferably a progressive spectacle lens, with regard to patients having an implanted intraocular lens. This object is achieved in particular by a computer-implemented method, a device, a computer program product, a storage medium, and a corresponding spectacle lens with the features specified in the independent claims. Preferred embodiments are the subject of the dependent claims.

A first aspect for solving the object relates to a computer-implemented method for identifying relevant individual parameters of at least one eye of a spectacle wearer for the calculation or optimization of a spectacle lens for the at least one eye of the spectacle wearer, wherein an intraocular lens was implanted in the at least one eye of the spectacle wearer as part of surgery, comprising the steps of:

providing individual refraction data on the at least one eye of the spectacle wearer;
defining an individual eye model in which at least
a shape and/or power of a cornea, in particular a corneal front surface, of a model eye;
a cornea-lens distance;
parameters of the lens of the model eye; and
a lens-retina distance are defined as parameters of the individual eye model, wherein defining the parameters of the individual eye model takes place on the basis of data on visual acuity correction of the at least one eye having the intraocular lens and further on the basis of individual measurement values for the eye of the spectacle wearer and/or standard values and/or on the basis of the provided individual refraction data such that the model eye has the provided individual refraction data.

In a preferred embodiment, the data for the visual acuity correction of the at least one eye having the intraocular lens include (in particular individual) intraocular lens data. Thus, in this embodiment, the parameters of the individual eye model are defined on the basis of intraocular lens data and further on the basis of individual measurement values for the eye of the spectacle wearer and/or standard values and/or on the basis of the provided individual refraction data so that the model eye has the provided individual refraction data, with the parameters of the lens of the model eye being defined on the basis of the intraocular lens data.

In a further preferred embodiment, a lens-retina distance of the eye of the spectacle wearer is identified, and the parameters of the individual eye model are defined on the basis of the identified lens-retina distance and further on the basis of individual measurement values for the eye of the spectacle wearer and/or standard values and/or on the basis of the provided individual refraction data such that the model eye has the provided individual refraction data, with the lens-retina distance of the model eye being defined by the identified lens-retina distance of the eye of the spectacle wearer. In other words, in this embodiment, the data for the visual acuity correction of the at least one eye having the intraocular lens includes an identified lens-retina distance.

In particular, the data for the visual acuity correction of the at least one eye having the intraocular lens can include an identified lens-retina distance and/or intraocular lens data.

Thus, the present invention in particular provides a computer-implemented method for identifying relevant individual parameters of at least one eye of a spectacle wearer for the calculation or optimization of a spectacle lens for the at least one eye of the spectacle wearer, with an intraocular lens having been implanted in the at least one eye of the spectacle wearer as part of surgery or the at least one eye of the spectacle wearer (in particular instead of or in addition to the natural eye lens) having an implanted intraocular lens, comprising the steps of:
providing individual refraction data on the at least one eye of the spectacle wearer; and
defining an individual eye model, in which at least
a shape and/or power of a cornea, in particular a corneal front surface, of a model eye;
a cornea-lens distance;
parameters of the lens of the model eye; and
a lens-retina distance;
are defined as parameters of the individual eye model, wherein:
a) defining the parameters of the individual eye model takes place on the basis of intraocular lens data and further on the basis of individual measurement values for the eye of the spectacle wearer and/or standard values and/or on the basis of the provided individual refraction data such that the model eye has the provided individual refraction data, wherein the parameters of the lens of the model eye are defined on the basis of the intraocular lens data; and/or
b) a lens-retina distance of the eye of the spectacle wearer is identified and defining the parameters of the individual eye model takes place on the basis of the identified lens-retina distance and further on the basis of individual measurement values for the eye of the spectacle wearer and/or standard values and/or on the basis of the provided individual refraction data such that the model eye has the provided individual refraction data, wherein the lens-retina distance of the model eye is defined by the identified lens-retina distance of the eye of the spectacle wearer.

The method can therefore comprise both the procedure defined under point a) and the procedure defined under point b). The procedure defined under point a) is preferably carried out if (in particular individual) intraocular lens data is known. Further preferably, the procedure defined under point b) is carried out if no intraocular lens data is known. In other words, the procedure defined under point a) is carried out in the case of known intraocular lens data, and the procedure defined under point b) is carried out in the case of unknown intraocular lens data. However, it is also possible that, in the case of known intraocular lens data, the procedure described under point b) be carried out (e.g. to avoid inconsistencies in advance and/or to only have to keep one algorithm or order channel available). It is also possible that, in the case of unknown intraocular lens data, the procedure defined under point a) be carried out by assuming certain intraocular lens data. In particular, the procedures defined under point a) and under point b) represent (mutually independent) alternative procedures of the method.

As an alternative, the method can also comprise either only the procedure defined under point a) or the procedure defined under point b). In the context of the procedure defined under point a), the individual intraocular lens data is in particular provided. The intraocular lens data can include or be known (e.g. measured or specified by the manufacturer) intraocular lens data. Alternatively or additionally, the intraocular lens data can comprise or be assumed intraocular lens data. In particular, the intraocular lens data is individual intraocular lens data.

The intraocular lens can in particular be an aphakic intraocular lens or a phakic intraocular lens. An aphakic intraocular lens replaces the natural eye lens, i.e. the at least one eye of the spectacle wearer only has the intraocular lens after surgery (but no longer the natural lens). A phakic intraocular lens, in contrast, is inserted or implanted in the at least one eye of the spectacle wearer in addition to the natural eye lens, i.e. the at least one eye of the spectacle wearer has both the intraocular lens and the natural eye lens after surgery.

In the context of the present invention, the term "lens of the model eye" can refer not only to a single real lens (e.g. the natural eye lens or an intraocular lens), but also to a lens system. The lens system can include one or more lenses, in particular two lenses (namely the natural lens of the eye and also an intraocular lens). In other words, in the context of the present invention, the "lens of the model eye" can be a lens, in particular a model-based or virtual lens, which describes the natural eye lens or an (aphakic) intraocular lens. Alternatively, in the context of the present invention, the "lens of the model eye" can also be a in particular model-based or virtual lens system, which describes the natural eye lens and additionally a (phakic) intraocular lens. For example, the "lens of the model eye" can be understood as a thick lens of the model eye (or the "lens of the model eye" can be a thick lens of the model eye), which combines and/or describes both the properties of the natural eye lens and the properties of an additional intraocular lens. In particular, in the context of the present invention, the term "lens of the model eye" is understood to mean a "lens system of the model eye". Correspondingly, in the context of the present invention, the term "lens-retina distance" is understood to mean in particular a "lens system-retina distance". For the sake of simplicity, however, only the terms "lens of the model eye" and "lens-retina distance" will be used in the following.

A phakic intraocular lens can e.g. be considered as an own/separate or additional element in the eye model. Alternatively, the power of a phakic intraocular lens can influence the power (or one of the surfaces or both surfaces) of the cornea. In this case, the intraocular lens can be an anterior chamber lens, for example. As a further alternative, the power of a phakic intraocular lens can influence the power (or one of the surfaces or in both surfaces) of the natural eye lens. In this case, the intraocular lens can be a posterior chamber lens, for example. If the intraocular lens is introduced as an additional element, its properties (in particular power, surfaces and/or thickness) can be taken into account in the eye model as additional parameters of the eye model. For example, the position of this additional lens can either be defined as a known position or taken into account as an additional parameter (e.g. measured or model-based) in the eye model. The defined position can (in the case of an anterior chamber lens) e.g. be directly or at a certain distance behind the cornea, or e.g. (in the case of a posterior chamber lens) directly or at a certain distance in front of the eye lens.

In particular, within the scope of the first aspect there is provided a computer-implemented method for identifying relevant individual parameters of at least one eye of a spectacle wearer for the calculation or optimization of a spectacle lens for the at least one eye of the spectacle wearer, the at least one eye of the spectacle wearer having an implanted intraocular lens, comprising the steps of:— providing intraocular lens data on the intraocular lens implanted in the eye of the spectacle wearer;
providing individual refraction data on the at least one eye of the spectacle wearer; and
defining an individual eye model, in which in particular at least
a shape and/or power of a cornea, in particular a corneal front surface, of a model eye;
a cornea-lens distance;
parameters of the lens of the model eye; and
a lens-retina distance;
are defined on the basis of the provided intraocular lens data and further on the basis of individual measurement values for the eye of the spectacle wearer and/or standard values and/or on the basis of the provided individual refraction data such that the model eye has the provided individual refraction data, wherein defining the parameters of the lens of the model eye is carried out on the basis of the provided intraocular lens data. Preferably, at least defining the lens-retina distance is carried out by calculation.

The spectacle lens can be optimized according to one of the methods described in WO 2013/104548°A1 or DE 10 2017 007 974 A1 by tracing into the eye. As described in DE 10 2017 007 975 A1 or WO 2018/138140 A2, the eye model required for this is assigned individual values, with the known properties of the IOL, e.g. from the manufacturer's information, being included in the lens of the eye model. The intraocular lens data includes data on properties of the implanted intraocular lens. These can be specified directly when ordering or obtained from a database by specifying the type or the individual serial number. This is helpful or advantageous, since the model-based values used in DE 10 2017 007 975 A1 or WO 2018/138140 A2 are not necessarily consistent with the properties of the lens actually implanted. This can be the case, for example, when a length myopia is at least partially compensated for by an IOL with less refraction. In this case, the method described in DE 10 2017 007 975 A1 or WO 2018/138140 A2 would result in too short an eye length.

The eye model preferably comprises various components such as cornea, lens, retina, etc. and parameters or a set of parameters of these components. Parameters of the eye model are e.g. the shape of a corneal front surface of the model eye, the cornea-lens distance, the parameters of the lens of the model eye, the lens-retina distance, etc.

In a preferred embodiment, the distance lens-retina (hereinafter DLR or $d_{LR}$) is calculated from the defocus term of the entire eye, the defocus term of the corneal surface, the distance cornea-lens (hereinafter DCL or $d_{CL}$) and the data on the IOL with one of the formalisms described in DE 10 2017 007 975 A1 or WO 2018/138140 A2. The term defocus term will be used below for the value of the symmetrical second term ($c_{2,0}$) of the Zernike decomposition of the refractive power or the surface of an optical element.

In particular, one or more of the following data can be used:
IOL data: This can either be the defocus of the refractive surfaces (front and back surface) and a propagation length (thickness of the lens, hereinafter DLL) or the defocus of the refractive power of the IOL. While a model based on the surfaces and the distance can deliver more precise results during optimization, optimization requires more calculation steps (refraction-propagation-refraction instead of just refraction) and correspondingly detailed information about the IOL, which may not be available.
Defocus term of the entire eye: The result of an aberrometric measurement or an autorefraction, a subjective refraction or another determination (e.g. retinoscopy) can be used here. Alternatively, a so-called "optimized refraction", i.e. the result of a calculation from several components (e.g. subjective refraction and aberrometry) can be used. Examples of such an optimization are compiled in DE 10 2017 007 975 A1 or WO 2018/138140 A2. In particular, the individual refraction data on the at least one eye of the spectacle wearer include a defocus or defocus term of the (overall) eye.
Defocus term of the cornea: It can be taken e.g. from a topography or topometry measurement or it can be assumed based on a model.
Distance cornea-lens: It can be determined with a measurement (e.g. Scheimpflug imaging or OCT) or assumed based on a model.

Instead of or in addition to the defocus, another variable, preferably a second-order term, such as the power in the main section with the highest or lowest refractive power or in a meridian with a defined position (e.g. horizontal or vertical) can be used.

Depending on requirements, the eye model can be supplemented by the astigmatism (magnitude and axis, or the other second-order variables according to the previous paragraph) as well as higher-order components (see DE 10 2017 007 975 A1 or WO 2018/138140 A2) of the entire eye and the components. These can be taken e.g. from the IOL data, measurements (e.g. topography/topometry or aberrometry/autorefraction), model assumptions and/or calculated values (e.g. optimized refraction).

Often, information about asphericity or higher-order aberrations is given for IOLs. These can be used when higher-order aberrations are assigned to the eye model.

First of all, individual refraction data on the at least one eye of the spectacle wearer are provided. This individual refraction data is based on an individual refraction determination. The refraction data includes at least the spherical and astigmatic vision disorder of the eye. In a preferred embodiment, the acquired refraction data also describes higher-order aberrations (HOA). Preferably, the refraction data (also referred to as aberrometric data in particular if they include higher-order aberrations) is measured by an optician, for example, using an autorefractometer or an aberrometer (objective refraction data). Alternatively or in addition, a subjectively determined refraction can be used as well. Subsequently, the refraction data will preferably be communicated to a lens manufacturer and/or provided to a calculation or optimization program. The data is therefore available to be acquired, in particular to be read out and/or received in digital form for the method according to the invention.

Preferably, providing the individual refraction data comprises providing or identifying the vergence matrix $S_M$ of the vision disorder of the at least one eye. Here, the vergence matrix describes a wavefront in front of the eye of the light emanating from a point on the retina or converging in a point on the retina. In terms of measurement technology, such refraction data can be determined e.g. by illuminating a point on the retina of the spectacle wearer by means of a laser, from which point light then propagates. While the light from the illuminated point initially diverges substantially spherically in the vitreous body of the eye, the wavefront can change when passing through the eye, in particular at optical boundary surfaces in the eye (e.g. the eye lens and/or the cornea). The refraction data on the eye can thus be measured by measuring the wavefront in front of the eye.

In addition, the method according to the first aspect of the invention comprises defining an individual eye model, which individually defines at least certain specifications about geometric and optical properties of a model eye. Thus, in the individual eye model according to the invention, at least a shape (topography) and/or power of the cornea, in particular of a corneal front surface of the model eye, a cornea-lens distance $d_{CL}$ (this distance between the cornea and a lens front surface of the model eye is also referred to as anterior chamber depth), parameters of the lens of the model eye, which in particular at least partially define the optical power of the lens of the model eye, and a lens-retina distance $d_{LR}$ (this distance between the lens, in particular the lens back surface, and the retina of the model eye is also referred to as the vitreous body length) is defined in a specific way, namely in such a way that the model eye has the provided individual refraction data, i.e. that a wavefront emanating in the model eye from a point on the retina of the model eye matches with the wavefront identified (e.g. measured or otherwise identified) for the real eye of the spectacle wearer (up to a desired accuracy). As parameters of the lens of the model eye (lens parameters), for example either geometric parameters (shape of the lens surfaces and their distance) and preferably material parameters (e.g. refractive indices of the individual components of the model eye) can be defined so completely that they at least partially define an optical power of the lens. Alternatively or in addition, parameters directly describing the optical power of the lens of the model eye can also be defined as lens parameters. With regard to the cornea, the shape of the corneal front surface is usually measured, but alternatively or in addition the power of the cornea as a whole (no differentiation between front and back surfaces) can be specified. A corneal back surface and/or a corneal thickness can possibly also be specified as well.

If individual intraocular lens data is known or provided, the parameters of the lens of the model eye can be defined (exclusively) on the basis of the provided intraocular lens data. In particular, the parameters of the lens of the model eye can correspond to the individual provided intraocular lens data. In other words, the provided intraocular lens data can be defined as the parameters of the lens of the model eye.

In the simplest case of an eye model, the refraction of the eye is determined by the optical system consisting of the corneal front surface, the eye lens, and the retina. In this simple model, the refraction of light on the corneal front surface and the refractive power of the eye lens (preferably including the spherical and astigmatic aberrations and higher-order aberrations) together with their positioning relative to the retina define the refraction of the model eye.

Here, the individual variables (parameters) of the model eye are defined accordingly on the basis of the provided intraocular lens data and further on the basis of individual measurement values for the eye of the spectacle wearer and/or on the basis of standard values and/or on the basis of the provided individual refraction data. In particular, some of the parameters (e.g. the topography of the corneal front surface and/or the anterior chamber depth and/or at least a curvature of a lens surface, etc.) can be provided directly as individual measurement values. Other values can also be taken over from values of standard models for a human eye, especially if the parameters involved are very complex to measure individually. Overall, however, not all (geometric) parameters of the model eye have to be specified from individual measurements or from standard models. Rather, in the context of the invention, an individual adaptation is carried out for one or more (free) parameters by performing a calculation taking into account the predefined parameters such that the then-resulting model eye has the provided individual refraction data. Depending on the number of parameters included in the provided individual refraction data, a corresponding number of (free) parameters of the eye model can be individually adapted (fitted). Deviating from a model proposed e.g. in WO°2013/104548°A1, at least the lens-retina distance can be defined by calculation in the context of the present invention.

For the calculation or optimization of the spectacle lens, a first surface and a second surface of the spectacle lens are specified in particular as starting surfaces with a predetermined (individual) position relative to the model eye. In a preferred embodiment, only one of the two surfaces is optimized. This is preferably the back surface of the spectacle lens. A corresponding starting surface is preferably specified for both the front surface and the back surface of the spectacle lens. In a preferred embodiment, however, only one surface is iteratively changed or optimized during the optimization process. The other surface of the spectacle lens can be a simple spherical or rotationally symmetrical aspherical surface, for example. However, it is also possible to optimize both surfaces.

Starting from the two predetermined surfaces, the method for calculating or optimizing comprises determining the path of a main ray through at least one visual point (i) of at least one surface of the spectacle lens to be calculated or optimized into the model eye. The main ray describes the geometric beam path emanating from an object point through the two spectacle lens surfaces, the corneal front surface, and the lens of the model eye preferably up to the retina of the model eye.

In addition, the method for calculating or optimizing according to this aspect of the invention comprises evaluating an aberration of a wavefront resulting from a spherical wavefront incident on the first surface of the spectacle lens along the main ray on an evaluation surface in particular in front of or within the model eye compared to a wavefront (reference light) converging in one point on the retina of the eye model.

In particular, a spherical wavefront ($w_0$) incident on the first surface (front surface) of the spectacle lens along the main ray is specified for this purpose. This spherical wavefront describes the light emanating from an object point (object light). The curvature of the spherical wavefront when incident on the first surface of the spectacle lens corresponds to the reciprocal of the object distance. The method thus preferably comprises specifying an object distance model that assigns an object distance to each viewing direction or to each visual point of the at least one surface of the spectacle lens to be optimized. This preferably describes the individual wearing situation in which the spectacle lens to be manufactured is to be used.

The wavefront incident on the spectacle lens is now refracted on the front surface of the spectacle lens preferably for the first time. The wavefront then propagates along the main ray within the spectacle lens from the front surface to the back surface, where it is refracted for the second time. Preferably, the wavefront transmitted through the spectacle lens now propagates along the main ray up to the corneal front surface of the eye, where it is preferably refracted again. Preferably, after further propagation within the eye up to the eye lens, the wavefront is also refracted again there in order to finally propagate preferably up to the retina of the eye. Depending on the optical properties of the individual optical elements (spectacle lens surfaces, corneal front surface, eye lens), each refraction process also leads to a deformation of the wavefront.

In order to achieve an exact mapping of the object point to an image point on the retina, the wavefront would preferably have to leave the eye lens as a converging spherical wavefront, the curvature of which corresponds exactly to the reciprocal value of the distance to the retina. A comparison of the wavefront emanating from the object point with a wavefront (reference light) converging in a point on the retina (in the ideal case of a perfect image) thus allows the evaluation of a mismatch. This comparison and thus the evaluation of the wavefront of the object light in the individual eye model can take place at different points along the path of the main ray, in particular between the second surface of the optimizing spectacle lens and the retina. In particular, the evaluation surface can thus be at different positions, in particular between the second surface of the spectacle lens and the retina. The refraction and propagation of the light emanating from the object point is calculated accordingly in the individual eye model, preferably for each visual point. The evaluation surface can either relate to the actual beam path or to a virtual beam path such as is used to construct the exit pupil AP, for example. In the case of the virtual beam path, the light must be propagated back through the back surface of the eye lens after refraction up to a desired level (preferably up to the level of the AP), wherein the refractive index used must correspond to the medium of the vitreous body and not to the eye lens. If the evaluation surface is provided behind the lens or after the refraction on the lens back surface of the model eye, or if the evaluation surface is reached by back-propagation along a virtual beam path (as in the case of the AP), then the resulting wavefront of the object light can preferably simply be compared to a spherical wavefront of the reference light. To this end, the method thus preferably comprises specifying a spherical wavefront incident on the first surface of the spectacle lens, identifying a wavefront resulting from the spherical wavefront due to the power at least of the first and second surfaces of the spectacle lens, the corneal front surface, and the lens of the model eye in the at least an eye, and evaluating the aberration of the resulting wavefront in comparison to a spherical wavefront converging on the retina.

If, however, an evaluation surface is to be provided within the lens or between the lens of the model eye and the spectacle lens to be calculated or optimized, a reverse propagation from a point on the retina through the individual components of the model eye up to the evaluation surface is simulated as the reference light, in order to make a comparison of the object light with the reference light there.

However, as already mentioned at the beginning, a complete correction of the refraction of the eye is generally not possible simultaneously for all viewing directions of the eye, i.e. for all visual points of the at least one spectacle lens surface to be optimized. Depending on the viewing direction, intentional maladjustment of the spectacle lens is thus preferably specified, which, depending on the application situation, is small especially in the mainly used zones of the spectacle lens (e.g. central visual points), and somewhat higher in the less-used zones (e.g. peripheral visual points). In principle, this procedure is already known from conventional optimization methods.

To optimize the spectacle lens, the at least one surface of the spectacle lens to be calculated or optimized is varied iteratively until an aberration of the resulting wavefront corresponds to a specified target aberration, i.e. in particular deviates from the wavefront of the reference light (e.g. a spherical wavefront whose center of curvature is on the retina) by specified values. The wavefront of the reference light is also referred to as a reference wavefront here. Preferably, the method comprises minimizing a target function F, in particular analogous to the target function described at the beginning. Further preferred target functions, in particular when taking higher-order aberrations into account, will be described further below. If a propagation of the object light up to the retina is calculated, an evaluation can be carried out there instead of a comparison of wavefront parameters, for example by means of a so-called "point spread function".

In the context of the present invention, it is therefore suggested, in particular for the calculation or optimization of a spectacle lens, that such an individual eye model that is individually adapted to the individual spectacle lens wearer up to the retina be defined that at least the vitreous body length of the model eye is calculated individually as a function of other individually identified, in particular measurement data on the eye. This parameter does not have to be defined a-prior, nor does it have to be measured directly. In the context of the present invention, it was found that this brought about a remarkable improvement in the individual adaptation with comparatively little effort, because the wavefront tracing turned out to be very sensitively dependent on this length parameter.

The individual calculation of the eye model, in particular the lens-retina distance (vitreous body length), can already be carried out e.g. in an aberrometer or a topograph with a correspondingly expanded functionality. Preferably, the length of an eye is identified individually. Particularly preferably, the measured and/or calculated vitreous body length and/or the identified (measured and/or calculated) eye length is displayed to the user. To this end, a corresponding device (in particular an aberrometer or topograph) has a corresponding display device.

In particular, in the context of the present invention, as far as available, known properties of the implanted IOLs can be used when calculating spectacle lenses. This advantageously results in a spectacle lens that is better adapted for patients with an implanted IOL and has optimized imaging and design preservation on the retina.

In a preferred embodiment, the intraocular lens data comprise at least a defocus of the front surface of the intraocular lens, a defocus of the back surface of the intraocular lens, and a thickness of the intraocular lens. Alternatively or in addition, the intraocular lens data includes at least a defocus of the refractive power of the intraocular lens or an optical power of the intraocular lens. The intraocular lens data can therefore either be the defocus of the refractive surfaces (front and back surfaces) and a propagation length (thickness of the lens, hereinafter DLL) or the defocus of the refractive power of the IOL. While a model based on the surfaces and the distance can deliver more precise results during optimization, optimization requires more calculation steps (refraction-propagation-refraction instead of just refraction) and correspondingly detailed information about the IOL, which may not be available. Alternatively or in addition, the intraocular lens data can include information, in particular a value, relating to a so-called A constant. The A constant is an individual lens constant, in particular a type of correction factor that can appear in IOL calculation formulae with different names. It is also known as the IOL constant or "surgeon factor". Each IOL from each manufacturer has a different A constant that is specified for each calculation formula. This constant represents the intraocular lens in the various calculation formulae. Since all IOL constants can be converted into one another, there is in principle only one constant (number) that is to characterize a given intraocular lens in the entire available power range, regardless of form factor, optical material, IOL diameter, etc. By using A or IOL constants, the effects of individual surgical technology, measurement and surgical equipment used, and individual physiological differences in the cohort of patients undergoing surgery on the IOL calculation are minimized. The A constant particularly reflects any adaptations in the power and can be part of the lens prescription or IOL prescription.

In a further preferred embodiment, the (individual) intraocular lens data is provided on the basis of type or serial number information, in particular by the manufacturer of the IOL. This information can be indicated e.g. directly when ordering or be obtained from a database.

In a further preferred embodiment, the method further comprises the steps of:
carrying out a consistency check of the defined eye model, and
solving any inconsistencies, in particular with the aid of analytical and/or numerical and/or probabilistic methods.

In any case, the procedure according to the invention provides a consistent model with regard to the defocus (or the other variables used in the calculation of the eye length). However, the consistency of the model is no longer ensured already with other second-order variables (e.g. magnitude and direction of the astigmatism). In other words, the eye model can be overdetermined and consequently no longer consistent. On the one hand, this can be due to manufacturing inaccuracies of the IOL and measurement inaccuracies, which can occur e.g in the topography or topometry, aberrometry or autorefraction and/or the measurement of the anterior chamber depth. On the other hand, when subjective refraction is used, inconsistencies can in principle arise if the subjective or optimized refraction does not correspond to the objective optical power of the entire eye. In the context of this description, a consistent eye model is understood to mean an eye model in which an incident wavefront that corresponds to the aberrations of the entire eye converges at a point on the retina. This is synonymous with the fact that the wavefront emanating from a point of light on the retina corresponds to the aberrations of the entire eye after it has passed through the entire eye.

A consistency check can in particular be carried out using probabilistic methods. In this case, a consistency measure could be given as a probability. Any inconsistencies could be solved e.g. by determining a maximum of the probability.

If, for example, a phakic intraocular lens, i.e. an artificial lens in addition to the existing natural eye lens, has been implanted in the at least one eye of the spectacle wearer, solving any inconsistencies can in particular comprise adapting one or more parameters of the eye model (or post-surgery eye model) modified or added due to the additional lens, if this is helpful or necessary to achieve the consistency of the eye model (or post-surgery eye model).

Carrying out a consistency check and solving any inconsistencies in particular improves the calculation or optimization of spectacle lenses intended for a patient with IOLs. However, carrying out a consistency check and solving any inconsistencies are also advantageous in the case of spectacle lenses not specifically intended for a patient with IOLs. The present invention thus generally provides a computer-implemented method for identifying relevant individual parameters of at least one eye of a spectacle wearer for the calculation or optimization of a spectacle lens for the at least one eye of the spectacle wearer, comprising the steps of:

providing individual refraction data on the at least one eye of the spectacle wearer;

defining an individual eye model, in which in particular one or more of the following information or parameters, namely a shape and/or power of a cornea, in particular a corneal front surface (18), of a model eye (12); and/or a cornea-lens distance; and/or parameters of the lens of the model eye; and/or a lens-retina distance; and/or a size of the entrance pupil; and/or a size and/or position of a physical aperture diaphragm (or iris opening) are defined on the basis of individual measurement values for the eye of the spectacle wearer and/or standard values and/or on the basis of the provided individual refraction data, carrying out a consistency check of the defined eye model, in particular with the provided individual refraction data, and optionally solving any inconsistencies, in particular with the aid of analytical and/or numerical and/or probabilistic procedures or methods.

If the eye model includes parameters of the cornea, the position and size of the aperture diaphragm of the eye can be converted into the position and size of the entrance pupil and vice versa, since the entrance pupil represents the aperture diaphragm imaged by the cornea. It can therefore in particular be sufficient if in this case the position or the size of either the aperture diaphragm or the entrance pupil is used as an (possibly additional) parameter of the eye model.

"Defining an individual eye model" can mean defining model parameters to be specific values. Additionally or alternatively, however, "defining an individual eye model" can also comprise defining at least one consistency measure (or at least one probability). In particular, a plurality of values of the model parameters can exist. A consistency measure or probability can be defined for each combination of these values. For example, such consistency measures or probabilities can be defined using Bayes' method.

Preferably, at least the defining of the lens-retina distance is carried out by calculation. The term "calculation" in the context of the present invention can include not only the calculation using an equation, but also steps that are carried out in a statistical method, such as the selection of values on the basis of statistical considerations or probabilities. With the Bayes' method, it is possible, for example, that only a likely or most likely lens-retina distance is selected or defined by an optimization problem (which then still has to be solved). The term "calculation" in the context of the present invention can thus in particular also include the selection of likely or most likely values of one or more parameters and/or the definition of an optimization problem. In particular, the term "calculation" also includes a selection, determination and/or definition in the context of a statistical procedure, e.g. in the context of or using the Bayes' method. The term "calculation" can in particular also include optimization.

In addition or as an alternative to performing a consistency check on the defined eye model and solving any inconsistencies, the computer-implemented method can also comprise defining or constructing a consistent eye model, in particular using Bayes' method and/or a maximum likelihood method. In other words, the individual eye model used or to be defined is a consistent eye model, with the consistency being made possible or established by statistical or probabilistic methods, in particular using Bayes' method and/or a maximum likelihood method.

In particular, in this aspect there is provided a computer-implemented method and a corresponding device for performing such a method for identifying relevant individual parameters of at least one eye of a spectacle wearer for the calculation or optimization of a spectacle lens for the at least one eye of the spectacle wearer, comprising one or more of the following steps or functions:

providing individual refraction data on the at least one eye of the spectacle wearer; and/or defining an individual eye model, in which in particular one or more of the following information or parameters, namely a shape and/or power of a cornea, in particular a corneal front surface, of a model eye; and/or a cornea-lens distance; and/or parameters of the lens of the model eye; and/or a lens-retina distance; and/or a size of the entrance pupil; and/or a size and/or position of a physical aperture diaphragm (or iris opening) are defined in particular on the basis of individual measurement values for the eye of the spectacle wearer and/or standard values and/or on the basis of the provided individual refraction data, wherein one or more of the information or parameters and/or at least partially the provided individual refraction data is or are initially defined in the form of a probability distribution, and wherein defining the individual eye model comprises identifying the model eye by identifying values for information or parameters within the defined probability distribution by a probabilistic method.

While in some aspects a model eye is first created by defining parameter values in order to then possibly modify the model eye on the basis of a consistency check using a probabilistic method so that the eye model is consistent, in the present case, instead of possibly inconsistent parameter values, a probability distribution is started for at least one parameter in order to then consistently identify the most likely parameter value and thus the most probably model eye using a probabilistic method. Parameters of the probability distribution(s), such as mean values and/or standard deviations, can in particular be determined on the basis of individual measurement values for the eye of the spectacle wearer and/or standard values and/or on the basis of the provided individual refraction data. Further details and specific exemplary embodiments of such methods will be described below.

In the following, a few examples are used to describe how any inconsistencies in the eye model can be eliminated by adapting the parameters with the aid of analytical calculations.

The simplest possibility is to transfer the deviations to an element or a component of the eye model (e.g. cornea, front surface of the IOL, back surface of the IOL, refractive power of the IOL). For example, the back surface of the IOL could (contrary to the manufacturer's instructions) be chosen so that the model is consistent. For this purpose (when the defocus term is used), after the calculation of DLR, first the astigmatism, in particular according to magnitude and direction (e.g. according to the method described in DE°10°2017°007°975°A1 or WO°2018/138140°A2) can be defined so that the eye model becomes consistent in terms of astigmatism.

Furthermore, higher-order components of this surface (e.g. with the help of the method described in DE°10°2017°007°975°A1 or WO°2018/138140°A2) can be defined in subsequent steps, for example, so that the eye model is also consistent in these components. Alternatively or in addition, the corneal surface could be adapted accordingly. This is particularly useful if only model-based information on the cornea or no information on astigmatism or higher-order components are available due to topometric measurements.

In a further preferred embodiment, any inconsistencies are solved by adapting or redefining one or more parameters of the eye model. Preferably, several parameters of the eye model are adapted and the adaptation is divided among the plurality of parameters of the eye model. For example, known deviations can be divided among several elements or components and/or several parameters of the eye model, e.g. the cornea, the front surface of the IOL, the back surface of the IOL, and/or the refractive power of the IOL. In the simplest case, fixed or predetermined factors or proportions can be assumed, e.g. 33% on the cornea and 67% on the lens. Alternatively or in addition, a physiologically based distribution can be used as well.

Alternatively or in addition, a further or new parameter can be added to the eye model and defined such that the eye model becomes consistent. For example, the shape of the corneal back surface of a model eye can be such a further parameter. In the case of toric lenses with fixed astigmatism, for example, the cylinder axis and/or a lateral shift or tilt can be selected so that the resulting astigmatism of the model eye corresponds to the specification (as best as possible).

Alternatively or in addition, the lengths DCL, DLL and/or DLR can be adapted. If necessary, the power of the entire eye can also be adjusted. Here, the target power of the spectacle lens can be changed accordingly in order to render the eye model consistent.

In a further preferred embodiment, the parameters of the eye model are determined with the aid of probabilistic methods, i.e. using probability calculations. For this purpose, in particular Bayesian statistics and/or a maximum likelihood algorithm can be used.

Instead of or in addition to the analytical calculation of the eye length on the basis of a set of parameters, in particular all known parameters (hereinafter input parameters) can be combined and the parameters of the eye model (hereinafter output parameters) can be determined with the aid of statistical methods such as maximum likelihood and Bayes. Here, one or more of the following information on at least individual input parameters can be used:

confidence in the correctness;

measurement and manufacturing accuracy;

fluctuation range in a collective or ensemble;

effect on the optimization of the spectacle lens.

A description of two such methods and specific examples will be given below in the detailed description.

In a further preferred embodiment, an initial distribution of parameters of the eye model and individual data on properties of the at least one eye are provided, the parameters of the individual eye model being determined on the basis of the initial distribution of parameters of the eye model and the individual data using probability calculations. In other words, an initial eye model and individual data on properties of the at least one eye are provided, the parameters of the individual eye model being determined on the basis of the initial eye model and the individual data using probability calculations.

In a further preferred embodiment, an eye length of the model eye is determined taking into account the measured and/or calculated lens-retina distance. Preferably, the identified eye length is displayed on a display device or display.

The method according to the invention described above relates in particular to the case that properties or data on the implanted intraocular lens, i.e. the intraocular lens data, are known. However, if this data is not known or if no individual intraocular lens data on the intraocular lens implanted in the at least one eye of the spectacle wearer can be provided, then it is proposed within the scope of this invention that a lens-retina distance of the eye of the spectacle wearer be identified, wherein defining the parameters of the individual eye model takes place on the basis of the identified lens-retina distance and further on the basis of individual measurement values for the eye of the spectacle wearer and/or standard values and/or on the basis of the provided individual refraction data such that the model eye has the provided individual refraction data, wherein the lens-retina distance of the model eye is defined by the identified lens-retina distance of the eye of the spectacle wearer. The provided individual refraction data on the at least one eye of the spectacle wearer is individual post-surgery refraction data of the at least one eye of the spectacle wearer. And the individual eye model is consequently a post-surgery eye model. According to this additional or alternative approach of the present invention, i.e. in the absence of direct knowledge of the properties of the implanted lens, conclusions on the properties of the implanted IOL(s) are drawn by measurements on the patient.

In particular, an additional or alternative approach to solving the object (namely in the event that properties or data on the implanted intraocular lens are not known) relates to a computer-implemented method for identifying relevant individual parameters of at least one eye of a spectacle wearer for the calculation or optimization of a spectacle lens for the at least one eye of the spectacle wearer, with an intraocular lens having been implanted in the at least one eye of the spectacle wearer as part of surgery, comprising the steps of:

providing individual post-surgery refraction data on the at least one eye of the spectacle wearer;
identifying a lens-retina distance (or an eye length) of the eye of the spectacle wearer; and
defining an individual post-surgery eye model, in which in particular at least
a shape and/or power of a cornea, in particular a corneal front surface, of a model eye of the post-surgery eye model;
a cornea-lens distance of the model eye of the post-surgery eye model;
parameters of the lens of the model eye of the post-surgery eye model; and
a lens-retina distance of the model eye of the post-surgery eye model;
are defined on the basis of the identified lens-retina distance (or the eye length) and further on the basis of individual measurement values for the eye of the spectacle wearer (identified prior to or after surgery) and/or standard values and/or on the basis of the provided individual post-surgery refraction data so that the model eye of the post-surgery eye model has the provided individual post-surgery refraction data, with the lens-retina distance of the model eye of the post-surgery eye model being defined by the identified lens-retina distance of the eye of the spectacle wearer.

The term surgery (German: Operation) is generally abbreviated as OP. The term "post-surgery" (German: Nach-OP) refers to a situation after surgery, while the term "pre-surgery" (German: Vor-OP) refers to a situation before surgery. For example, the surgery is a cataract surgery in which the natural eye lens is replaced by an intraocular lens. However, it can also be a surgery on an aphakic eye (eye without a lens) in which an intraocular lens is inserted or implanted in the patient's eye. The intraocular lens can therefore in particular represent a replacement for the natural eye lens. In particular, the natural lens of the wearer's eye has been replaced by an intraocular lens during surgery. However, it is also possible that an artificial intraocular lens be placed in the at least one eye of the spectacle wearer in addition to the natural eye lens. The term surgery thus also includes the insertion or implantation of an artificial lens in addition to the natural lens of the eye.

The spectacle lens is preferably optimized according to one of the methods described in WO°2013/104548°A1 or DE°10°2017°007°974°A1 by tracing into the eye. By analogy with the description in DE 10 2017 007 975 A1 or WO 2018/138140 A2, the eye model required for this is assigned individual values. In this case, however, no information about the IOL is available and model-based values are not necessarily consistent with the actually implanted lens. This can be the case, for example, if a length myopia is at least partially compensated for by an IOL with less refraction. In this case, the eye length would be assumed to be too short according to the procedure described in DE 10 2017 007 975 A1 or WO 2018/138140 A2. Therefore, based on data that corresponds to a situation in which the original lens was located in the eye, the eye length or a lens-retina distance, as described in DE 10 2017 007 975 A1 or WO 2018/138140 A2, will be calculated.

Subsequently, the other parameters (i.e. the parameters of the eye lens, in this case the implanted IOL) will be determined on the basis of the thus-calculated eye length (or the calculated lens-retina distance) and the post-surgery values for the aberrations of the entire eye, the surface of the cornea, and the distance cornea-lens such that the power of this eye model corresponds to the aberrations of the entire eye. This differs fundamentally from the procedure in DE 10 2017 007 975 A1 or WO 2018/138140 A2 in that all values of the lens (in this case the implanted IOL) are determined and that not as in DE 10 2017 007 975 A1 or WO 2018/138140 A2 a second-order term (e.g. defocus) is already known. After determination of this term, however, further terms can be determined as described in DE 10 2017 007 975 A1 or WO 2018/138140 A2. These can be further second-order terms and possibly (e.g. in further steps) higher-order terms.

For the calculation of the eye length or lens-retina distance, the following data is preferably used specifically:
defocus of the entire eye before replacement of the lens: This can be the result of an aberrometric measurement or an autorefraction, a subjective refraction or another determination (e.g. retinoscopy) before the surgical procedure. Alternatively, a so-called "optimized refraction", i.e. the result of a calculation from several components (e.g. subjective refraction and aberrometry) can be used. Examples of such an optimization are compiled in DE 10 2017 007 975 A1 or WO 2018/138140 A2. Furthermore, the defocus of the refractive power of older spectacles worn before the surgical procedure can be used;

model-based values for the refractive power or the structure of the eye lens;
measured or model-based values for the cornea-lens distance; and
measured or model-based values for the defocus of the cornea.

The data on the last two points can be either from measurements before the surgical procedure (operation) or after the surgical procedure. The use of data determined after the surgical procedure is particularly useful if no corresponding measurements have been carried out before the surgical procedure.

By analogy, the following data is preferably used to calculate properties of the lens:—
aberrations of the entire eye after replacement of the lens: These can be the result of an aberrometric measurement or an autorefraction, a subjective refraction or another determination (e.g. retinoscopy) after the surgical procedure. Alternatively, a so-called "optimized refraction", i.e. the result of a calculation from several components (e.g. subjective refraction and aberrometry) can be used. Examples of such an optimization are compiled in DE 10 2017 007 975 A1 or WO 2018/138140 A2.
the previously determined distance lens-retina;
measured or model-based values for the distance cornea-lens; and
measured or model-based values for the aberrations of the cornea.

The data on the last two points can be either from measurements before the surgical procedure (operation) or after the surgical procedure. The use of data determined before the surgical procedure is particularly useful if no corresponding measurements have been carried out after the surgical procedure.

Providing individual intraocular lens data can in particular comprise the following steps of:
identifying an eye length on the basis of data corresponding to a situation in which the original natural lens was still in the eye of the spectacle wearer (situation before the intraocular lens was implanted);
calculating the individual intraocular lens data on the basis of the identified eye length, the provided individual refraction data, measured or model-based values for the cornea-lens distance, and measured or model-based values for aberrations of the cornea.

The following table exemplarily includes three scenarios. It is understood, however, that other combinations are also part of the invention.

| Scenario | Values for first step (Calculation of DCL) Data to be transmitted | Values for second step (Substitution of the parameters that are still open) |
|---|---|---|
| 1 | Only data (aberrometry, topography, possibly distance cornea-lens, possibly subjective refraction) from before surgery (e.g. from an order) Reference number of the order before surgery, data (aberrometry, topography, possibly distance cornea-lens, subjective refraction) from after surgery (e.g. from an order) | Only data (aberrometry, topography, possibly distance cornea-lens, subjective refraction) from after surgery (e.g. from an order) |
| 2 | Only subjective refraction/values of the spectacles from before surgery Topography and, if necessary, distance cornea-lens before surgery | Only data (aberrometry, topography, possibly distance cornea-lens, subjective refraction) from after surgery (e.g. from an order) |
| 3 | Subjective refraction/values of the spectacles from before surgery as well as data (aberrometry, topography, possibly distance cornea-lens, subjective refraction) from after surgery (e.g. from an order) Only data (aberrometry, topography, possibly distance cornea-lens, possibly subjective refraction) from before surgery (e.g. from an order) Reference number of the order before surgery, subjective refraction from after surgery | Only subjective refraction from after surgery, further data (topography, possibly distance cornea-lens) from before surgery |

The determination of a lens-retina distance or an eye length of the eye of the spectacle wearer can take place by direct measurement, for example.

In a preferred embodiment, the method further comprises providing individual pre-surgery refraction data on the at least one eye of the spectacle wearer, wherein the determination of a lens-retina distance or an eye length of the eye of the spectacle wearer on the basis of an individual pre-surgery eye model takes place using the provided individual pre-surgery refraction data.

In a preferred embodiment, in the pre-surgery eye model, particularly at least
a shape and/or power of a cornea, in particular a corneal front surface, of a model eye of the pre-surgery eye model;
a cornea-lens distance of the model eye of the pre-surgery eye model;
parameters of the lens of the model eye of the pre-surgery eye model; and
a lens-retina distance of the model eye of the pre-surgery eye model
are defined on the basis of individual measurement values for the eye of the spectacle wearer (determined before or after surgery) and/or standard values and/or on the basis of the provided individual pre-surgery refraction data such that the model eye has the provided individual pre-surgery refraction data, wherein at least defining the lens-retina distance takes place by calculating.

The corneal front surface is preferably measured individually and the eye lens of the individual pre-surgery eye model is calculated accordingly in order to meet the individually determined pre-surgery refraction data. Here, in a preferred embodiment, the corneal front surface (or its curvature) is measured individually along the main sections (topometry). In a further preferred embodiment, the topography of the corneal front surface (i.e. the complete description of the surface) is measured individually. In a further preferred embodiment, the cornea-lens distance is defined on the basis of individual measurement values for the cornea-lens distance.

Particularly preferably, defining the parameters of the lens of the pre-surgery model eye comprises defining the following parameters:
a shape of the lens front surface;
a lens thickness; and
a shape of the lens back surface.

Even if it is not essential for the use of the invention, it is possible to further improve the individual adaptation using this more precise model of the lens.

In this case, in a particularly preferred embodiment, defining the lens thickness and the shape of the lens back surface takes place on the basis of predetermined values (standard values, for example from the technical literature), wherein defining the shape of the lens front surface further preferably comprises:

providing standard values for a mean curvature of the lens front surface; and calculating the shape of the lens front surface taking into account the provided individual refraction data.

In a further preferred embodiment of the more detailed lens model, defining the shape of the lens front surface comprises:

providing an individual measurement value of a curvature in a normal section of the lens front surface.

In this case, it is particularly preferred that defining the lens thickness and the shape of the lens back surface take place on the basis of standard values, and even more preferably defining the shape of the lens front surface comprises:

calculating the shape of the lens front surface taking into account the provided individual refraction data and the provided individual measurement value of the curvature in a normal section of the lens front surface.

As an alternative or in addition to the shape of the lens or the lens surfaces, defining the lens parameters can include defining an optical power of the lens. In particular, at least one position of at least one main plane and a spherical power (or at least one focal length) of the lens of the model eye are defined. A cylindrical power (magnitude and axial position) of the lens of the model eye is also particularly preferred. In a further preferred embodiment, optical higher-order aberrations of the lens of the model eye can also be identified.

Another independent aspect for solving the object relates to a computer-implemented method for calculating or optimizing a spectacle lens for at least one eye of a spectacle wearer, comprising:

a method for identifying relevant individual parameters of the at least one eye of the spectacle wearer according to the present invention;

specifying a first surface and a second surface for the spectacle lens to be calculated or optimized;

identifying the course of a main ray through at least one visual point of at least one surface of the spectacle lens to be calculated or optimized into the model eye;

evaluating an aberration of a wavefront resulting from a spherical wavefront incident on the first surface of the spectacle lens along the main ray on an evaluation surface compared to a wavefront converging in one point on the retina of the eye model;

iteratively varying the at least one surface of the spectacle lens to be calculated or optimized until the evaluated aberration corresponds to a predetermined target aberration.

Another independent aspect for solving the object relates to a computer-implemented method for calculating or optimizing a spectacle lens for at least one eye of a spectacle wearer, comprising:

a method according to the invention for identifying relevant individual parameters of the at least one eye of the spectacle wearer;

specifying a first surface and a second surface for the spectacle lens to be calculated or optimized;

identifying the course of a main ray through at least one visual point of at least one surface of the spectacle lens to be calculated or optimized into the model eye;

evaluating an aberration of a wavefront resulting from a spherical wavefront incident on the first surface of the spectacle lens along the main ray on an evaluation surface compared to a wavefront converging in one point on the retina of the eye model;

iteratively varying the at least one surface of the spectacle lens to be calculated or optimized until the evaluated aberration corresponds to a predetermined target aberration.

Preferably, the evaluation surface is located between the corneal front surface and the retina. In a particularly preferred embodiment, the evaluation surface is located between the lens and the retina of the model eye. In another particularly preferred embodiment, the evaluation surface is located on the exit pupil (AP) of the model eye. Here, the exit pupil can be located in front of the lens back surface of the model eye. With this positioning, a particularly precise, individual adaptation of the spectacle lens can be achieved.

Another independent aspect for solving the object relates to a method for producing a spectacle lens, comprising:

calculating or optimizing a spectacle lens according to the inventive method for calculating or optimizing a spectacle lens; and manufacturing the thus-calculated or optimized spectacle lens.

Furthermore, the invention provides a device for identifying relevant individual parameters of at least one eye of a spectacle wearer for the calculation or optimization of a spectacle lens for the at least one eye of the spectacle wearer, comprising:

at least one data interface for providing individual data on properties of the at least one eye of the spectacle wearer; and a modeling module for defining an individual eye model, which in particular at least defines a shape and/or power of a cornea, in particular a corneal front surface (18), of a model eye (12);

a cornea-lens distance;

parameters of the lens of the model eye; and a lens-retina distance on the basis of individual measurement values for the eye of the spectacle wearer and/or standard values and/or on the basis of the provided individual refraction data, wherein at least defining the lens-retina distance takes place by calculating; and wherein the modeling module is configured to carry out a consistency check of the defined eye model with the provided individual refraction data and to solve any inconsistencies, in particular with the aid of analytical and/or probabilistic methods.

Another independent aspect for solving the object relates to a device for identifying relevant individual parameters of at least one eye of a spectacle wearer for the calculation or optimization of a spectacle lens for the at least one eye of the spectacle wearer, the at least one eye of the spectacle wearer having an implanted intraocular lens, comprising:

at least one data interface for providing individual intraocular lens data on the intraocular lens implanted in the eye of the spectacle wearer and for providing individual refraction data on the at least one eye of the spectacle wearer; and a modeling module for defining an individual eye model, which in particular at least defines a shape and/or power of a cornea, in particular a corneal front surface (18), of a model eye;

a cornea-lens distance;

parameters of the lens of the model eye; and a lens-retina distance as parameters of the individual eye model, wherein defining the parameters of the individual eye model takes place on the basis of data on visual acuity correction of the at least one eye having the intraocular lens and further on the basis of individual measurement values for the eye of the spectacle wearer and/or standard values and/or on the basis of the provided individual refraction data such that the model eye has the provided individual refraction data.

In a preferred embodiment, the parameters of the individual eye model are defined on the basis of intraocular lens data and further on the basis of individual measurement values for the eye of the spectacle wearer and/or standard values and/or on the basis of the provided individual refraction data so that the model eye (12) has the provided individual refraction data, with the parameters of the lens of the model eye being defined on the basis of the intraocular lens data.

In a further preferred embodiment, the modeling module is configured to identify a lens-retina distance of the eye of the spectacle wearer. Furthermore, the parameters of the individual eye model are defined on the basis of the identified lens-retina distance and further on the basis of individual measurement values for the eye of the spectacle wearer and/or standard values and/or on the basis of the provided individual refraction data such that the model eye has the provided individual refraction data, the lens-retina distance of the model eye being defined by the identified lens-retina distance of the eye of the spectacle wearer.

In particular, the invention provides a device for identifying relevant individual parameters of at least one eye of a spectacle wearer for the calculation or optimization of a spectacle lens for the at least one eye of the spectacle wearer, at least one eye of the spectacle wearer having an implanted intraocular lens, comprising:
  at least one data interface for providing individual refraction data on the at least one eye of the spectacle wearer; and
  a modeling module for defining an individual eye model, which in particular at least defines
    a shape and/or power of a cornea, in particular a corneal front surface, of a model eye;
    a cornea-lens distance;
    parameters of the lens of the model eye; and
    a lens-retina distance
as parameters of the individual eye model, wherein:
  a) defining the parameters of the individual eye model takes place on the basis of intraocular lens data and further on the basis of individual measurement values for the eye of the spectacle wearer and/or standard values and/or on the basis of the provided individual refraction data such that the model eye has the provided individual refraction data, wherein the parameters of the lens of the model eye are defined on the basis of the intraocular lens data; and/or
  b) a lens-retina distance of the eye of the spectacle wearer is identified by the modeling module and defining the parameters of the individual eye model takes place on the basis of the identified lens-retina distance and further on the basis of individual measurement values for the eye of the spectacle wearer and/or standard values and/or on the basis of the provided individual refraction data such that the model eye has the provided individual refraction data, wherein the lens-retina distance of the model eye is defined by the identified lens-retina distance of the eye of the spectacle wearer.

The device or the modeling module can be configured to carry out both procedure a) and procedure b). Alternatively, however, the device can also be configured to carry out either only the procedure defined under point a) or the procedure defined under point b). In the first case a), the data interface is in particular configured to provide the intraocular lens data in addition to the individual refraction data on the at least one eye of the spectacle wearer.

In particular, another independent approach to solving the object relates to a device for identifying relevant individual parameters of at least one eye of a spectacle wearer for the calculation or optimization of a spectacle lens for the at least one eye of the spectacle wearer, the at least one eye of the spectacle wearer having an implanted intraocular lens (in particular instead of in addition to the natural eye lens), comprising:
  at least one data interface for providing individual intraocular lens data on the intraocular lens implanted in the eye of the spectacle wearer and for providing individual refraction data on the at least one eye of the spectacle wearer; and
  a modeling module for defining an individual eye model, which in particular at least defines
    a shape and/or power of a cornea, in particular a corneal front surface, of a model eye;
    a cornea-lens distance;
    parameters of the lens of the model eye; and
    a lens-retina distance
on the basis of the provided intraocular lens data and further on the basis of individual measurement values for the eye of the spectacle wearer and/or standard values and/or on the basis of the provided individual refraction data such that the model eye has the provided individual refraction data, wherein defining the parameters of the lens of the model eye is carried out on the basis of the provided intraocular lens data. Preferably, defining the lens-retina distance is carried out by measuring and/or calculating.

Preferably, the modeling module is configured to identify an eye length of the model eye taking into account the measured and/or calculated lens-retina distance. The device preferably also comprises a display device for displaying the measured and/or calculated lens-retina distance and/or the determined eye length. The device is particularly preferably designed as an aberrometer and/or as a topograph.

Preferably, the modeling module is configured to carry out a consistency check of the identified eye model, in particular the identified pre-surgery eye model and/or the identified post-surgery eye model. Furthermore, the modeling module is preferably configured to solve any inconsistencies, in particular with the aid of analytical and/or probabilistic methods (probability calculation, e.g. using Bayesian statistics and/or a maximum likelihood approach).

In particular, within the scope of the present invention there is provided a device for identifying relevant individual parameters of at least one eye of a spectacle wearer for the calculation or optimization of a spectacle lens for the at least one eye of the spectacle wearer, with an intraocular lens being implanted in the at least one eye of the spectacle wearer during surgery, and wherein the device comprises:
  at least one data interface for providing individual post-surgery refraction data on the at least one eye of the spectacle wearer; and
  a modeling module for identifying a lens-retina distance of the eye of the spectacle wearer and for defining an individual post-surgery eye model, which in particular at least defines
    a shape and/or power of a cornea, in particular a corneal front surface, of a model eye of the post-surgery eye model;

a cornea-lens distance of the model eye of the post-surgery eye model;
parameters of the lens of the model eye of the post-surgery eye model; and
a lens-retina distance of the model eye of the post-surgery eye model
on the basis of the determined lens-retina distance and further on the basis of individual measurement values for the eye of the spectacle wearer (identified before or after surgery) and/or standard values and/or on the basis of the provided individual post-surgery refraction data such that the model eye of the post-surgery eye model has the provided individual post-surgery refraction data, wherein the lens-retina distance of the model eye of the post-surgery eye model is defined by the identified lens-retina distance of the spectacle wearer's eye.

Another independent aspect for solving the object relates to a device for calculating or optimizing a spectacle lens for at least one eye of a spectacle wearer, comprising:
a device according to the invention for identifying relevant individual parameters of the at least one eye of the spectacle wearer;
a surface model database for specifying a first surface and a second surface for the spectacle lens to be calculated or optimized;
a main ray identification module for identifying the course of a main ray through at least one visual point of at least one surface of the spectacle lens to be calculated or optimized into the model eye;
an evaluation module for evaluating an aberration of a wavefront resulting from a spherical wavefront incident on the first surface of the spectacle lens along the main ray on an evaluation surface compared to a wavefront converging in one point on the retina of the eye model; and
an optimization module for iteratively varying the at least one surface of the spectacle lens to be calculated or optimized until the evaluated aberration corresponds to a predetermined target aberration.

Another independent aspect for solving the object relates to a device for producing a spectacle lens, comprising:
calculation or optimization means configured to calculate or optimize the spectacle lens according to an inventive method for calculating or optimizing a spectacle lens; and
machining means configured to machine the spectacle lens in accordance with the result of the calculation or optimization.

The device for producing a spectacle lens can be designed in one piece or as an independent machine, i.e. all components of the device (in particular the calculation or optimization means and the machining means) can be part of one and the same system or one and the same machine. In a preferred embodiment, however, the device for producing a spectacle lens is not designed in one piece, but is realized by different (in particular independent) systems or machines. For example, the calculation or optimization means can be realized as a first system (in particular comprising a computer) and the machining means as a second system (in particular a machine comprising the machining means). Here, the different systems can be located in different places, i.e. they can be locally separated from one another. For example, one or more systems can be located in the front end and one or more other systems in the back end. The individual systems can e.g. be located at different company locations or operated by different companies. The individual systems in particular have communication means in order to exchange data with one another (for example via a data carrier). Preferably, the various systems of the device can communicate with one another directly, in particular via a network (e.g. via a local network and/or via the Internet). The above statements regarding the device for producing a spectacle lens do not only apply to this device, but also generally to all of the devices described in the context of the present invention. In particular, a device described herein can be designed as a system. The system can in particular comprise several devices (possibly locally separated) configured to carry out individual method steps of a corresponding method.

In addition, the invention offers a computer program product or a computer program article, in particular in the form of a storage medium or a data stream containing program code that is designed, when loaded and executed on a computer, to execute a method according to the invention for identifying relevant individual parameters of at least one eye of a spectacle wearer and/or to execute a method according to the invention for calculating or optimizing a spectacle lens. In particular, a computer program product is to be understood as a program stored on a data carrier. In particular, the program code is stored on a data carrier. In other words, the computer program product comprises computer-readable instructions that, when loaded into a memory of a computer and executed by the computer, cause the computer to execute a method according to the invention.

Furthermore, the invention provides a spectacle lens produced by a method according to the invention and/or using a device according to the invention.

In addition, the invention provides a use of a spectacle lens produced by the production method according to the present invention, in particular in a preferred embodiment, in a predetermined average or individual wearing position of the spectacle lens in front of the eyes of a specific spectacle wearer for correcting a vision disorder of the spectacle wearer.

The invention can in particular comprise one or more of the following aspects:
the spectacle lens as a product;
the calculation and manufacture of the spectacle lens;
the calculation of properties (in particular of designs and surfaces) of the spectacle lens;
the calculation of the eye length and the assignment to an eye model (also for purposes other than lens calculation);
a method, a device and/or a system for acquiring the relevant data, e.g. in the form of or as part of ordering and/or industry software, in particular for manual input and/or for importing from measuring devices and/or databases;
a method, a device and/or a system, in particular a protocol, for the transmission of the relevant data;
a method, a device and/or a system for storing the relevant data, which can be different from the method, the device and/or the system for calculating the spectacle lens;
a method, a device and/or a system for providing and retrieving the data on the IOLs, in particular on the basis of type or serial number information by the manufacturer of the IOL, the calculator of the spectacle lens, or a third party;
devices and computer program products for implementing the above points.

In particular, a computer-implemented method according to the invention can be provided in the form of ordering and/or industry software. In particular, the data required for the calculation and/or optimization and/or manufacture of a spectacle lens, in particular the intraocular lens data and/or the prescription data and/or the individual refraction data (pre-surgery and/or post-surgery refraction data) of the at least one eye of the spectacle wearer, can be acquired and/or transmitted. The intraocular lens data can be transmitted e.g. from the manufacturer of the intraocular lens data to the calculator and/or manufacturer of the spectacle lens. The prescription data and/or individual refraction data can be transmitted e.g. from the optician and/or ophthalmologist or surgeon to the calculator and/or manufacturer of the spectacle lens. Alternatively or in addition, it may be possible to retrieve this data from a database, in particular with the help of a type and/or serial number of the implanted IOL or with the help of a patient code (e.g. customer or patient number, name, etc.). Measurement or refraction data can also be called up directly from a measuring device, for example. A common transmission protocol or a transmission protocol specially developed for the method according to the invention can be used for the transmission of the data. As an alternative or in addition, the data to be transmitted can also be input, at least in part, manually via an input unit. In this way, an ophthalmologist or surgeon can e.g. transmit the so-called A constant or IOL constant of the intraocular lens used. In particular, a lens or IOL prescription can also be created semi- or fully automatically on the basis of the transmitted data.

A device according to the invention and/or a system according to the invention, e.g. for ordering a spectacle lens, can in particular comprise a computer and/or data server configured to communicate via a network (e.g. Internet). The computer is in particular configured to execute a computer-implemented method, e.g. ordering software for ordering at least one spectacle lens, and/or transmission software for transmitting relevant data (in particular intraocular lens data and/or prescription data and/or refraction data), and/or identification software for identifying relevant individual parameters of at least one eye of a spectacle wearer, and/or calculation or optimization software for calculating and/or optimizing a spectacle lens to be produced, according to the present invention.

The statements made above or below regarding the embodiments of the first aspect also apply to the above-mentioned further independent aspects or approaches and in particular to preferred embodiments in this regard. In particular, the statements made above and below on the embodiments of the respective other independent aspects also apply to an independent aspect of the present invention and to preferred embodiments in this regard.

BRIEF DESCRIPTION OF THE DRAWINGS

Preferred embodiments and examples of the invention will be explained below by way of example, at least in part with reference to the accompanying drawings, which show.

DETAILED DESCRIPTION

Figure 1:
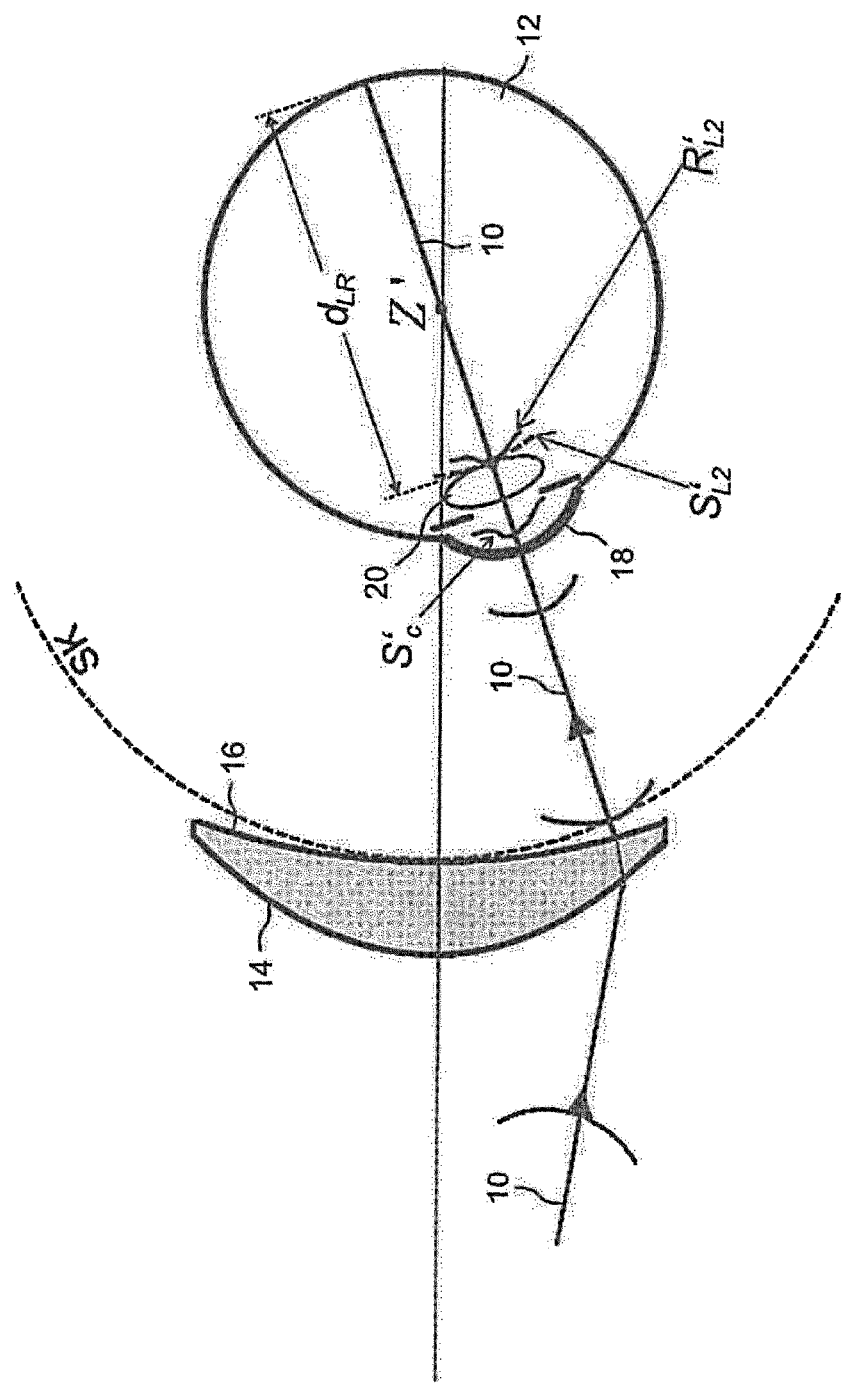
FIG. 1 a schematic representation of the physiological and physical model of a spectacle lens and an eye together with a beam path in a predetermined wearing position.

FIG. 1 shows a schematic representation of the physiological and physical model of a spectacle lens and an eye in a predetermined wearing position together with an exemplary beam path on which an individual spectacle lens calculation or optimization according to a preferred embodiment of the invention is based.

Here, only a single ray is preferably calculated for each visual point of the spectacle lens (the main ray 10, which preferably runs through the ocular center of rotation Z), but also the derivatives of the vertex depths of the wavefront according to the transverse coordinates (perpendicular to the main ray). These derivatives are taken into account up to the desired order, the second derivatives describing the local curvature properties of the wavefront and the higher derivatives being related to the higher-order aberrations.

Upon light tracing through the spectacle lens up to the eye 12 according to the individually provided eye model, the local derivatives of the wavefronts are ultimately identified at a suitable position in the beam path in order to compare them there with a reference wavefront that converges in a point on the retina of the eye 12. In particular, the two wavefronts (i.e. the wavefront coming from the spectacle lens and the reference wavefront) are compared with one another in an evaluation surface.

"Position" does not simply mean a certain value of the z-coordinate (in the direction of light), but such a coordinate value in combination with the specification of all surfaces through which refraction took place before reaching the evaluation surface. In a preferred embodiment, refraction takes place through all refractive surfaces including the lens back surface. In this case, the reference wavefront is preferably a spherical wavefront whose center of curvature is located on the retina of the eye 12.

It is particularly preferred not to propagate any further after this last refraction, so that the radius of curvature of this reference wavefront does correspond to the distance between the lens back surface and the retina. In a further preferred embodiment, propagation is still carried out after the last refraction, preferably up to the exit pupil AP of eye 12. This is, for example, at a distance $$d_{AR} = d_{LR}^{(b)} = d_{LR} - d_{LR}^{(a)} > d_{LR}$$

in front of the retina and thus even in front of the lens back surface, so that the propagation in this case is a back propagation (the designations $d_{LR}^{(a)}$, $d_{LR}^{(b)}$ will be described below in the listing of steps 1-6). In this case, too, the reference wavefront is spherical with the center of curvature on the retina, but has a radius of curvature $1/d_{AR}$.

To this end, it is assumed that a spherical wavefront $w_0$ emanates from the object point and propagates up to the first spectacle lens surface 14. There it is refracted and then it propagates to the second lens surface 16, where it is refracted again. The wavefront $w_{g1}$ exiting the spectacle lens then propagates along the main ray in the direction of the eye 12 (propagated wavefront $w_{g2}$) until it hits the cornea 18, where it is refracted again (wavefront $w_c$). After further propagation within the anterior chamber of the eye up to the eye lens 20, the wavefront is also refracted again by the eye lens 20, whereby the resulting wavefront $w_e$ arises on the back surface of the eye lens 20 or on the exit pupil of the eye, for example. This is compared with the spherical reference wavefront $w_s$ and the deviations are evaluated for all visual points in the target function (preferably with corresponding weightings for the individual visual points).

Thus, the vision disorder is no longer described only by a thin sphero-cylindrical lens, as was customary in many conventional methods, but rather the corneal topography, the eye lens, the distances in the eye, and the deformation of the wavefront (including the low-order aberrations—i.e. sphere, cylinder and cylinder axis—as well as preferably including the higher-order aberrations) are directly taken into account in the eye. Here, the vitreous body length $d_{LR}$ is calculated individually in the eye model according to the invention.

An aberrometer measurement preferably provides the individual wavefront deformations of the real eye having the visual defect for distance and near (deviations, no absolute refractive indices) and the individual mesopic and photopic pupil diameters. From a measurement of the corneal topography (surface measurement of the corneal front surface), an individual real corneal front surface is preferably obtained, which generally makes up almost 75% of the total refractive power of the eye. In a preferred embodiment, it is not necessary to measure the corneal back surface. It is preferably described by an adaptation of the refractive index of the cornea and not by a separate refractive surface due to the small refractive index difference compared to the aqueous humor and because of the small cornea thickness in a good approximation.

In general, in this description, bold lowercase letters are intended to denote vectors and bold capital letters are intended to denote matrices, such as the (2×2) vergence matrices or refractive index matrices $$S = \begin{pmatrix} S_{xx} & S_{xy} \\ S_{xy} & S_{yy} \end{pmatrix}, \ C\begin{pmatrix} C_{xx} & C_{xy} \\ C_{xy} & C_{yy} \end{pmatrix}, \ L = \begin{pmatrix} L_{xx} & L_{xy} \\ L_{xy} & L_{yy} \end{pmatrix}, \ 1 = \begin{pmatrix} 1 & 0 \\ 0 & 1 \end{pmatrix}$$

and italics like d are intended to denote scalar quantities.

Furthermore, bold, italicized capital letters are intended to denote wavefronts or surfaces as a whole. For example, *S* is the vergence matrix of the wavefront S of the same name, except that *S* besides the 2nd order aberrations summarized in S, also comprises the entirety of all higher-order aberrations (HOA) of the wavefront. From a mathematical point of view, *S* stands for the set of all parameters necessary to describe a wavefront (with sufficient accuracy) in relation to a given coordinate system. Preferably, *S* stands for a set of Zernike coefficients with a pupil radius or a set of coefficients of a Taylor series. Particularly preferably, *S* stands for the set of a vergence matrix S for describing the wavefront properties of the 2nd order and a set of Zernike coefficients (with a pupil radius), which is used to describe all remaining wavefront properties except the 2nd order, or a set of coefficients according to a Taylor decomposition. Analogous statements apply to surfaces instead of wavefronts.

Among other things, the following data can be measured directly in principle:
The wavefront $S_M$, which is generated by the laser spot on the retina and the passage through the eye (from aberrometric measurement)—
Shape of the corneal front surface C (through corneal topography)—
Distance between cornea and lens front surface $d_{CL}$ (by pachymetry). This variable can also be determined indirectly by measuring the distance between the cornea and the iris; correction values can be applied if necessary here. Such corrections can be the distance between the lens front surface and the iris from known eye models (e.g. literature values).
Curvature of the lens front surface in a direction $L_{1,xx}$ (by pachymetry) In this case, without restricting generality, the x-plane can be defined exemplarily such that this section lies in the x-plane. If the coordinate system is defined such that this plane is inclined, the derivative must be supplemented by the functions of the corresponding angle. It is not required that this be a main section. For so example, it can be the section in the horizontal plane.

Furthermore, the following data—depending on the embodiment—can either be measured or taken from the literature:
Thickness of the lens $d_L$
Curvature of the lens back surface in the same direction as the lens front surface $L_{2,xx}$ (by pachymetry)
Thus, there are the following options for the lens back surface:
Measurement of $L_{2,xx}$ ($L_{2,M}$) and assumption of a rotational symmetry $$L_{2,xx} = L_{2,yy} = L_2 = L_{2,M}$$

and $L_{2,xy} = L_{2,yx} = 0$
Taking $L_{2,xx}$ from the literature ($L_{2,Lit}$) and assumption of a rotational symmetry $$L_{2,xx} = L_{2,yy} = L_2 = L_{2,M}$$

und $L_{2,xy} = L_{2,yx} = 0$
Taking the complete (asymmetrical) form $L_2$ from the literature ($L_{2,Lit}$)
Measurement of $L_{2,xx}$ ($L_{2,M}$) and assumption of a cylinder or an otherwise specified asymmetry $a_{Lit}$ from the literature $L_{2,xx} = L_{2,M}$ und $$L_{2,xy} = L_{2,yx} = f(L_{2,xx}, a_{Lit})$$

and $L_{2,yy} = g(L_{2,xx}, a_{Lit})$
The following data can be found in the literature:
Refractive indices $n_{CL}$ of the cornea and anterior chamber of the eye as well as the aqueous humor $n_{LR}$ and that of the lens $n_L$
This leaves in particular the distance $d_{LR}$ between the lens back surface and the retina and the components $L_{1,yy}$ and $L_{1,xy} = L_{1,yx}$ of the lens front surface as unknown parameters. To simplify the formalism, the former can also be written as a vergence matrix $D_{LR} = D_{LR} \cdot 1$ with $D_{LR} = n_{LR}/d_{LR}$. Furthermore, the variable τ is generally used, which is defined as τ=d/n (whereby for the refractive index, always the corresponding index must be used as n, as for d and τ, e.g. as $\tau_{LR} = d_{LR}/n_{LR}$, $\tau_{CL} = d_{CL}/n_{CL}$).

The modeling of the passage of the wavefront through the eye model used according to the invention, i.e. after passage through the surfaces of the spectacle lens, can be described as follows in a preferred embodiment in which the lens is described via a front and a back surface, with the transformations the vergence matrices is explicitly being specified:
1. Refraction of the wavefront S with the vergence matrix S on the cornea C with the surface power matrix C to the wavefront S'$_C$ with vergence matrix S'$_C$=S+C
2. Propagation around the anterior chamber depth $d_{CL}$ (distance between cornea and lens front surface) to wavefront $S_{L1}$ with vergence matrix $S_{L1}$=S'$_C$/(1−$\tau_{CL}$·S')

$$S_{L1} = \frac{S'_C}{(1 - \tau_{CL} \cdot S'_C)}$$

3. Refraction on the lens front surface $L_1$ with the surface power matrix $L_1$ to the wavefront $S'L_1$ with the vergence matrix $S'_{L1}=S_{L1}+L_1$
4. Propagation around the lens thickness $d_L$ to the wavefront $S_{L2}$ with vergence matrix $S_{L2}=S'_{L1}/(1-\tau_L \cdot S'_{L1})$
5. Refraction on the lens back surface $L_2$ with the surface power matrix $L_2$ to the wavefront $S'_{L2}$ with vergence matrix $S'_{L2}=S_{L2}-L_2$
6. Propagation around the distance between lens and retina $d_{LR}$ to wavefront $S_R$ with the vergence matrix $SS_R=S'_{L2}/(1-\tau_{LR} \cdot S'_{L2})$ Each of the steps 2, 4, 6, in which the distances $\tau_{CL}$, $\tau_{CL}$, and $\tau_{CL}$ are propagated, can be divided into two partial propagations 2a, b), 4a, b) or 6a, b) according to the following scheme, which explicitly reads for step 6a, b):

6a. Propagation around the distance $d_{LR}^{(a)}$ between the lens and the intermediate plane to the wavefront $S_{LR}$ with the vergence matrix $S_{LR}=S'_{L2}/(1-\tau_{LR}^{(a)}S'_{L2})$
6b. Propagation around the distance $d_{LR}^{(b)}$ between the intermediate plane and the retina to the wavefront $S_R$ with the vergence matrix $S_R=S_{LR}/(1-\tau_{LR}^{(b)}S_{LR})$ Here, $\tau_{LR}^{(a)}=d_{LR}^{(a)}/n_{LR}^{(a)}$ and $\tau_{LR}^{(b)}=d_{LR}^{(b)}/n_{LR}^{(b)}$ can be positive or negative, whereby it should always hold that $$n_{LR}^{(a)} = n_{LR}^{(b)} = n_{LR}$$

and $\tau_{LR}^{(a)}+\tau_{LR}^{(b)}=\tau_{LR}$. In any case, steps 6a and 6b can be combined again by $$S_R = S'_{L2}/\left(1 - \left(\tau_{LR}^{(a)} + \tau_{LR}^{(b)}\right)S'_{L2}\right) = S'_{L2}/(1 - \tau_{LR}S'_{L2}).$$

The division in steps 6a and 6b offers advantages, however, and the intermediate plane can preferably be placed in the plane of the exit pupil AP, which preferably is located in front of the lens back surface. In this case $\tau_{LR}^{(a)}<0$ and $\tau_{LR}^{(b)}>0$.

The division of steps 2, 4 can be analogous to the division of step 6 in 6a, b).

Decisive for the choice of the evaluation surface of the wavefront is not only the absolute position in relation to the z-coordinate (in the direction of light), but also the number of surfaces through which refraction took place up to the evaluation surface. Thus, one and the same level can be passed several times. For example, the plane of the AP (which normally is located between the lens front surface and the lens back surface) is formally passed by the light for the first time after an imaginary step 4a, in which propagation takes place from the lens front surface by the length $\tau_L^{(a)}>0$. The same plane is reached for the second time after step 6a when, after the refraction through the lens back surface, propagation back to the AP plane takes place, i.e. $\tau_{LR}^{(a)}=-\tau_L+\tau_L^{(a)}=-\tau_L^{(b)}<0$, which is synonymous with $\tau_{LR}^{(a)}=\tau_{LR}^{(b)}<0$. In the case of the wavefronts $S_{AP}$ that refer to the AP in the text, the wavefront $S_{AP}=S_{LR}$ that is the result of step 6a should preferably always be meant (unless explicitly stated otherwise).

Reference will be made to these steps 1 to 6 again in the further course of the description. They describe a preferred relationship between the vergence matrix S of a wavefront S on the cornea and the vergence matrices of all intermediate wavefronts resulting therefrom at the refractive intermediate surfaces of the eye, in particular the vergence matrix $S'_{L2}$ of a wavefront $S'_{L2}$ after the eye lens (or even a wavefront $S_R$ on the retina). These relationships can be used both to calculate parameters that are not known a priori (e.g. $d_{LR}$ or $L_1$) and thus to assign values to the model either individually or generically, and to simulate the propagation of the wavefront in the eye for optimizing spectacle lenses with the models that underwent assignment.

In a preferred embodiment, the surfaces and wavefronts are treated up to the second order, for which a representation by means of vergence matrices is sufficient. Another preferred embodiment described later takes into account and also uses higher orders of aberrations.

In a description in the second order, the eye model, in a preferred embodiment, has twelve parameters as degrees of freedom of the model that have to undergo assignment. These preferably include the three degrees of freedom of the surface power matrix C of the cornea C, the three degrees of freedom of the surface power matrices $L_1$ and $L_2$ for the front and back surfaces of the lens, as well as respectively one for the length parameters anterior chamber depth $d_{CL}$, lens thickness $d_L$, and the vitreous body length $d_{LR}$.

In principle, these parameters can undergo assignment in several ways:
i. Directly, i.e. individual measurement of a parameter
ii. Value of a parameter given a priori, e.g. as a literature value or from an estimate, for example due to the presence of a measurement value for another variable, which correlates in a known manner with the parameter to be determined on the basis of a previous population analysis
iii. Calculation from consistency conditions, e.g. compatibility with a known refraction The total number $df_2$ of degrees of freedom of the eye model in the second order (df stands for 'degree of freedom', index '2' for second order) is thus composed of:

$$df_2=df_2(i)+df_2(ii)+df_2(iii)$$

For example, if there are direct measurement values for all twelve model parameters, then $df_2(i)=12$, $df_2(ii)=0$ and $df_2(iii)=0$, which will be expressed by the notation $df_2=12+0+0$ in the following for the sake of simplicity. In such a case, the objective refraction of the relevant eye is also defined, so that an objective refraction determination no longer has to be carried out in addition.

A central aspect of the invention relates precisely to the airm of not having to measure all parameters directly. In particular, it is significantly easier to measure the refraction of the relevant eye or to determine it objectively and/or subjectively than to measure all parameters of the model eye individually. Preferably, there is thus at least one refraction, i.e. measurement data for the wavefront $S_M$ of the eye up to the second order, which corresponds to the data on the vergence matrix $S_M$. If the eye model undergoes assignment on the basis of purely objectively measurement data, these values can be taken from aberrometric measurements or autorefractometric measurements or, according to (ii), be assigned with other given data. Consideration of subjective methods (i.e. subjective refraction), be it as a replacement for the objective measurement of the refraction or by combining both results, will be described later. The three conditions of conformance with the three independent parameters of the vergence matrix $S_M$ thus make it possible to derive three parameters of the eye model, which corresponds to $df_2(iii)=3$ in the notation introduced above.

The invention therefore makes use of the possibility, in cases in which not all model parameters are accessible to direct measurements or in which these measurements would be very complex, to assign the missing parameters in a useful way. For example, if direct measurement values $(df_2(i) \leq 9)$ are available for a maximum of nine model parameters, then the refraction conditions mentioned can be used to calculate three of the model parameters $(df_2(iii)=3)$. If exactly $df_2(i)=9$, then all twelve model parameters are uniquely determined by the measurements and the calculation, and it holds that $(df_2(ii)=0)$. If, on the other hand, $df_2(i)<9$, then $df_2(ii)=9-df_2(i)>0$, i.e. the model is underdetermined in the sense that $df_2(ii)$ parameters must be defined a priori.

With the provision of an individual refraction, i.e. measurement data on the wavefront $S_M$ of the eye, in particular up to the second order, the necessary data on the vergence matrix $S_M$ are correspondingly available. According to a conventional method described in WO°2013/104548°A1, in particular the parameters $\{C, d_{CL}, S_M\}$ are measured. In contrast, the two length parameters $d_L$ and $d_{LR}$ (or $D_{LR}$) are conventionally defined a priori (e.g. by literature values or estimates). In WO°2013/104548°A1, a distinction is in particular made between the two cases in which either $L_2$ is defined a priori and $L_1$ is calculated therefrom, or vice versa. The aforementioned laid-open publication discloses Eq. (4) and Eq. (5) as a calculation rule. For both cases, it holds that $df_2=4+5+3$.

In the terminology used in steps 1 to 6 above, $L_1$ is adapted to the measurements in particular by calculating the measured vergence matrix $S_M$ by means of steps 1, 2 through the likewise measured matrix C and propagating it up to the object-side side of the lens front surface. On the other hand, a spherical wave is calculated back to front from an imaginary point-like light source on the retina by means of steps 6, 5, 4 carried out backward by refracting this spherical wave at the previously defined surface power matrix $L_2$ of the lens back surface and propagating the then-obtained wavefront from the lens back surface up to the image-side side of the lens front surface. The difference of the thus-determined vergence matrices $S_{L1}$ and $S'L_1$, which are located on the object side or on the image side of the lens front surface, must have been caused by the matrix $L_1$, since in the aberrometric measurement the measured wavefront emerges from a wavefront that emanates from a point pm the retina, and therefore, due to the reversibility of the beam paths, is identical to the incident wavefront $(S=S_M)$ that converges on this point of the retina. This leads to equation (4) in the laid-open publication mentioned:

$$L_1(D_{LR}) = \frac{D_{LR} \cdot 1 - L_2}{1 + \tau_L \cdot (D_{LR} \cdot 1 - L_2)} - \frac{S_M + C}{1 - \tau_{CL}(S_M + C)} \quad (1a)$$

The other case in the cited laid-open publication relates to the adaptation of the matrix $L_2$ to the measurements after the matrix $L_1$ has been defined. The only difference now is that the measured wavefront $S_M$ is subjected to steps 1, 2, 3, 4 and the assumed wavefront from the point-like light source only to step 6, and the missing step to be carried out to adapt the lens back surface $L_2$ is now step 5, according to equation (5) of the above-mentioned laid-open publication:

$$L_2 = D_{LR} - \left(\frac{S_M + C}{1 - \tau_{CL}(S_M + C)} + L_1\right)\left(1 - \tau_L\left(\frac{S_M + C}{1 - \tau_{CL}(S_M + C)} + L_1\right)\right)^{-1} \quad (1b)$$

The central idea of the invention is to calculate at least the length parameter $d_{LR}$ (or $D_{LR}$) from other measurement data and a priori assumptions about other degrees of freedom and not to assume it a priori itself, as is conventional. In the context of the present invention, it turned out that this brought about a remarkable improvement in the individual adaptation with comparatively little effort since the wavefront tracing turned out to be very sensitive to this length parameter. This means that it is an advantage according to the invention if at least the length parameter $d_{LR}$ belongs to the $df_2(iii)=3$ parameters that are calculated. In particular, it is difficult to measure this parameter directly, it varies more strongly between different test subjects, and these variations have a comparatively strong influence on the imaging of the eye.

The data on the vergence matrix $S_M$ and particularly preferably also the data on C are preferably available from individual measurements. In a further preferred aspect, which is preferably also taken into account in the following embodiments, in the assumption of data on the lens back surface, a spherical back surface, i.e. a back surface without astigmatic components is taken as a basis.

In a preferred embodiment of the invention, measurement data up to the second order are available for the cornea C, which corresponds to the data on the surface power matrix C. Although these values can be taken from topographical measurements, the latter are not necessary. Rather, topometric measurements are sufficient. This situation corresponds to the case $df_2=3+6+3$, with the anterior chamber depth $d_{CL}$ in particular being one of the six parameters to be defined a priori.

If no further individual measurements are made, the situation is $df_2=3+6+3$. In order to be able to uniquely determine $d_{LR}$, six parameters from $\{L_1, L_2, d_L, d_{CL}\}$ have to undergo assignment by assumptions or literature values. The other two result in addition to $d_{LR}$ from the calculation. In a preferred embodiment, the parameters of the lens back surface, the mean curvature of the lens front surface, and the two length parameters $d_L$ and $d_{CL}$ undergo assignment a priori (as predetermined standard values).

In a case that is particularly important for the invention, the anterior chamber depth $d_{CL}$, i.e. the distance between the cornea and the lens front surface, is also known e.g. from pachymetric or OCT measurements. The measured parameters thus include $\{C, d_{CL}, S_M\}$. This situation corresponds to the case $df_2=4+5+3$. The problem is therefore still underdetermined mathematically, so five parameters from $\{L_1, L_2, d_L\}$ have to be defomed a priori through assumptions or literature values. In a preferred embodiment, these are the parameters of the lens back surface, the mean curvature of the lens front surface, and the lens thickness.

For the accuracy of the individual adaptation alone, it is advantageous to be able to assign individual measurements to as many parameters as possible. In a preferred embodiment, the lens curvature is additionally provided in a normal section on the basis of an individual measurement. This then results in a situation according to $df_2=5+4+3$, and it is sufficient to define four parameters from $\{L_{yy}, \alpha_{L1}, L_2, d_L\}$ a priori. Here, too, in a preferred embodiment, the parameters of the lens back surface and the lens thickness are involved. The exact calculation will be described below.

In particular, as an alternative to the normal section of the lens front surface and particularly preferably in addition to the anterior chamber depth, the lens thickness can also be made available from an individual measurement. This eliminates the need to assign model data or estimated parameters to this parameter (df$_2$=5+4+3).

Otherwise, what has already been said above applies. This embodiment is particularly advantageous if a pachymeter is used, the measuring depth of which allows the lens back surface to be recognized, but not a sufficiently reliable determination of the lens curvatures.

In addition to the anterior chamber depth and a normal section of the lens front surface, one (e.g. measurement in two normal sections) or two further parameters (measurement of both main sections and the axial position) of the lens front surface can be obtained by an individual measurement. This additional information can be exploited in two ways in particular:

- Abandonment of a priori assumptions: One or two of the assumptions otherwise made a priori can be abandoned and determined by calculation. In this case the situations df$_2$=6+3+3 and df$_2$=7+2+3 arise. In the first case, the mean curvature of the back surface (assuming an astigmatism-free back surface) and in the second case the surface astigmatism (including cylinder axis) with given mean curvature can be determined. Alternatively, the lens thickness can also be determined from the measurements in both cases.

- However, such a procedure generally requires a certain degree of caution, since noisy measurement data can easily lead to the released parameters "running away". As a result, the model can become significantly worse instead of better overall. One possibility to prevent this is to specify anatomically sensible limit values for these parameters and to limit the variation of the parameters to this range. Of course, these limits can also be specified as a function of the measurement values.

- Reduction of the measurement uncertainty: If, on the other hand, the same a priori assumptions are made (preferably {L$_2$, d$_L$}), the situations df$_2$=6+4+3 and df$_2$=7+4+3 exist, the system is therefore mathematically overdetermined.

- Instead of a simple analytical determination of D$_{LR}$ according to the following explanations, D$_{LR}$ (and possibly the missing parameter from L$_1$) is determined ("fit") such that the distance between L$_1$ resulting from the equations and the measured L$_1$ (or L$_1$ supplemented by the missing parameter) becomes minimal. By this procedure—obviously—a reduction in the measurement uncertainty can be achieved.

In a further preferred implementation, the anterior chamber depth, two or three parameters of the lens front surface, and the lens thickness are measured individually. The other variables are calculated in the same way, whereby the a priori assumption of the lens thickness can be replaced by the corresponding measurement.

In a further preferred implementation, individual measurements of the anterior chamber depth, at least one parameter of the lens front surface, the lens thickness, and at least one parameter of the lens back surface are provided. This is an addition to the cases mentioned above. The respective additionally measured parameters can be carried out analogously to the step-by-step expansions of the above sections. These cases are particularly advantageous if the above-mentioned pachymetry units, which measure in one plane, two planes or over the entire surface, are correspondingly expanded in the measuring depth and are so precise that the curvature data can be identified with sufficient accuracy.

If the formula (1b) already mentioned above is solved for D$_{LR}$ in order to calculate the lens back surface for a given eye length (where D$_{LR}$=n$_{LR}$/d$_{LR}$ is the inverse vitreous body length d$_{LR}$ multiplied by the refractive index n$_{LR}$), namely $$L_2 = D_{LR} - \left(\frac{S_M + C}{1 - \tau_{CL}(S_M + C)} + L_1\right)\left(1 - \tau_L\left(\frac{S_M + C}{1 - \tau_{CL}(S_M + C)} + L_1\right)\right)^{-1}$$

one obtains $$D_{LR} = L_2 + \left(\frac{S_M + C}{1 - \tau_{CL}(S_M + C)} + L_2\right) \times \left(1 - \tau_L\left(\frac{S_M + C}{1 - \tau_{CL}(S_M + C)} + L_2\right)\right)^{-1}$$

for calculating D$_{LR}$. Since D$_{LR}$ is a scalar, all quantities for the calculation must also be taken as scalar. Preferably, S$_M$, C, L$_1$ and L$_2$ are each the spherical equivalents of the vision disorder, the cornea, the lens front surface, and the lens back surface, respectively. Once the vitreous body length d$_{LR}$ has been calculated (and thus the eye length as d$_A$=d$_C$+d$_{CL}$+d$_L$+d$_{LR}$), one of the surfaces can be modified again with regard to the cylinder and the HOA, preferably the lens front surface L1, in order to adapt it consistently.

For the calculation, the values of the so-called Bennett & Rabbetts eye for the refractive powers of the lens surfaces can be used, which can be taken from Table 12.1 of the book "Bennett & Rabbets' Clinical Visual Optics", third edition, by Ronald B. Rabbetts, Butterworth-Heinemann, 1998, ISBN-10: 0750618175, for example. The calculation described above leads to results that are very compatible with the population statistics, which state that short-sighted vision disorders tend to lead to large eye lengths and vice versa (see e.g. C. W. Oyster: "The Human Eye", 1998). The calculation described is, however, even more precise, since a direct use of the correlation from the population statistics can lead to unphysical values for the eye lens, which is avoided by the method according to the invention. Precise knowledge of the lens parameters is all the more important for a method in which these are assumed to be given. For example, if a customer had a vision disorder of −10 dpt before his cataract surgery, he must have an eye length between 28 mm and 30 mm. After surgery, however, due to his emmetropia, an eye length of 24 mm would be concluded, which does not match the actual eye length.

Preferred embodiments of the invention will be explained below.

Examples Using Bayesian Statistics

The aim of the method using Bayesian statistics is to use, if possible, all available information sources about an eye or a pair of eyes in a consistent manner in order to achieve an optimal correction of the eye or the eyes with an ophthalmic lens (e.g. a spectacle lens) in the light of this information.

As a rule, this information is incomplete and/or imprecise, which so far has often led to the fact that only simplified eye models are used to calculate ophthalmic lenses. Such a simplified eye model is e.g. an eye that is characterized solely by its refraction, since this can be determined with a certain accuracy (e.g. with an error of ±0.75 dpt in the spherical equivalent). However, if one wishes to use more complex eye models to calculate ophthalmic lenses, it makes sense to include information about the length of the eye, as well as the position and curvature of the refractive surfaces of the cornea and eye lens in the calculation, but this should only be taken into account as much as is possible within the scope of its accuracy.

In Bayesian statistics (see e.g. D. S. Sivia: "Data Analysis—A Bayesian Tutorial", Oxford University Press, 2006, ISBN-13: 978-0198568322 or ET Jaynes: "Probability Theory", Cambridge University Press, 2003, ISBN-13: 978-0521592710), information is always described in the form of probability distributions (in the case of continuous parameters it is probability densities).

In this sense, a probability or probability density can be assigned to an individual eye model with a given set of parameters. Individual eye models that are consistent with the available information (e.g. objective wavefront measurement and biometrics of the eye) have a higher probability or probability density, because e.g. the propagation and refraction of a wavefront that a point light source would generate on the retina after exiting the eye reproduces the measured data well within the scope of the measurement accuracy of the objective wavefront measurement, and likewise the parameters of the individual eye match with the available information about the biometry of the eye within the scope of the distributions known e.g. from the literature. Individual eye models that are not consistent with the available information are correspondingly assigned to low probabilities or probability densities. The probability or probability density of an individual eye model can be written as $$prob(\vartheta_i|d_i,I)$$

where $\vartheta_i$ denotes the parameters of the individual eye model i, and $d_i$ are the measured data (it can e.g. include the current refraction or the refraction measured prior to eye surgery, the measured shape and/or refractive properties of the cornea, the measured eye length or other variables measured on the individual eye). With I, the current state of knowledge upon evaluation of the data, i.e. the existing background information (e.g. about the measurement process of the refraction, the distribution of the parameters of the individual eye model or other related variables in the population) is summarized. The vertical line '|' means that the distribution of the variables to the left of '|' is meant for given (i.e. fixed) variables to the right of '|'.

The information obtained in the measurement process, in which the data $d_i$ is measured, can also be understood as the probability distribution of the data $d_i$ with given parameters $\vartheta_i$ of the individual eye model i:

$$prob(d_i|\vartheta_i,I)$$

The accuracy of the measurement process is reflected in the width of the distribution:

an exact measurement has a narrower distribution than an imprecise measurement, which has a wide or wider distribution of the data $d_i$.

Now, if one wishes to calculate the distribution of the parameters of an individual eye with given data and background information, the following proportionality can be used:

$$prob(\vartheta_i|d_i,I) \propto prob(\vartheta_i|I)prob(d_i|\vartheta_i,I)$$

The term $prob(\vartheta_i|I)$ describes the background knowledge about the parameters of the individual eye model. This can be information from literature, for example, but also information from data from past measurements. This can be data from the same person for whom the ophthalmic lens is to be manufactured, as well as data from measurements made for a large number of other people.

The probability here serves as a measure of consistency. Parameter values of the individual eye model that are consistent with the measurements can be found in particular where both $prob(\vartheta_i|I)$ and $prob(d_i|d_i,I)$ are high.

The probability or probability density $prob(\vartheta_i|d_i,I)$ can also be suitably normalized in order to write the proportionality as an equation.

The term $prob(\vartheta_i|d_i,I)$ can also include parameters of the eye lens. For example, some of the parameters $\vartheta_i$ can include the refractive power of the eye lens, its position and/or orientation in the eye, or other variables such as the refractive index and curvatures or shape of the surfaces.

The eye lens can be a natural lens. In this case, literature data on the parameters of natural eye lenses can be used (e.g. distributions of the curvatures of the front and/or back surface, refractive index, etc.).

If the eye lens is an intraocular lens, the distributions of the parameters of natural eye lenses must not be used. Instead, the parameters of the intraocular lens should be used, provided they are individually known. Otherwise, distributions of these parameters can be used from literature studies of eyes that underwent surgery. If such information is not available, a flat distribution within reasonable limits can be selected. For parameters that are positively definite and define length scales (e.g. radii of curvature or distances), it is also possible to select distributions that are flat in the logarithm of these parameters.

Formally, the cases "natural eye lens" or "intraocular lens as eye lens" are to be described by different states of background knowledge I (i.e. $I=I_{NL}$bzw$\cdot I=I_{IOL}$).

The probability or probability density prob $prob(\vartheta_i|d_i,I)$ can have one or more factors. Here, ach factor represents the information about one or more parameters of the individual eye model. For example, the distribution of different independent parameters $\vartheta_i^1$ and $\vartheta_i^2$ from different literature sources can be represented as a product $$prob(\vartheta_i \mid d_i, I) = prob(\vartheta_i^1, \vartheta_i^2 \mid d_i, I) = prob(\vartheta_i^1 \mid d_i, I)prob(\vartheta_i^2 \mid d_i, I).$$

By $prob(\vartheta_i|I)$, parameters of the eye model can inadvertently be falsified. For example, if the "true" refraction is understood as a parameter of the individual eye model, the most likely value of the "true" refraction can deviate from the measured refraction. If this is not desired, a distribution that is constant in the corresponding parameter (e.g. spherical equivalent of refraction) within carefully selected limits (e.g. between −30 dpt and +20 dpt for the spherical equivalent M, ±5 dpt for the astigmatic components $J_0$ and $J_{45}$) should be chosen.

If parameters of the individual eye model or other variables related to the parameters or measurement data is known exactly or with a high degree of accuracy, their distribution can be approximated as a Dirac delta distribution. The equations in these parameters or variables can be integrated on both sides, which may simplify subsequent calculations.

Description of the Methods

Two possible methods for calculating an ophthalmic lens will be presented below (Bayes A and Bayes B). In the Bayes A method, the available information is used to set up a (single) individual eye model, with the help of which an ophthalmic lens optimal for this eye model is calculated. The eye model can e.g. be given by or assigned the set of parameters $\vartheta_i^{max}$, which maximizes the probability or probability density $prob(\vartheta_i|d_i,I)$. Other sets of parameters can also be selected, e.g. the expected value $\langle \vartheta_i \rangle$ or the median $\vartheta_i^{med}$ of the parameters $\vartheta_i$ with regard to the distribution prob($\vartheta_i|d_i$,I).

The Bayes B method is more advantageous—but computationally more demanding—compared to Bayes A, since a subset of individual eye models with different sets of parameters can lead to ophthalmic lenses that have very similar (even identical) properties (e.g. refractive power in a reference point of the ophthalmic lens, or the distribution of the refractive deficit across a given area of the ophthalmic lens, or similar criteria for determining the quality of an ophthalmic lens). Overall, an ophthalmic lens that was not calculated with the most likely individual eye model can therefore represent an optimal correction for a subset of individual eye models which overall have a higher probability than the most likely individual eye model. It is therefore advantageous to search for the ophthalmic lens that optimally corrects the distribution of eye models, instead of just determining the most likely individual eye model and manufacturing an ophthalmic lens for it.

In both methods, an ophthalmic lens (e.g. a spectacle lens) consistent with the information available can be calculated.

Bayes A Method

In particular, one or more of the following steps can be carried out:—
- Providing an initial distribution of parameters of an eye model (ideally as a multivariate probability distribution of all parameters of the eye model, possibly also marginal distributions; the probability distribution corresponds to the information about the distribution of the parameters of the eye model in the population of the persons);
- Providing already known (in the best case measured) data on properties of an individual eye (ideally with probability distribution or measurement errors; the probability distribution corresponds to the inaccuracy of the measurements) The already known data can include: already known current subjective and/or objective refraction, already known previous subjective and/or objective refraction (e.g. prior to surgery), power and/or shape and/or position (most important is the axial position) of certain refractive surfaces of the eye, size and/or shape and/or position of the entrance pupil, refractive index of the refractive media, refractive index profile in the refractive media, opacity; possibly determination of these variables depending on the accommodation of the eye on a fixation object (target) at a given close distance;
- Determining the parameters of an individual eye model based on the initial distribution of the parameters of the eye model and the already known or measured data on the individual eye using probability calculation. Ideally, the probability distribution or, for example, the set of parameters characterizing a maximum of the probability distribution is determined.
- In particular, calculation methods such as Markov Chain Monte Carlo, Variational Inference, Maximum Likelihood, Maximum Posterior, or Particle Filter can be used;
- The aim here is to select the parameters of the individual eye model that are consistent both with the initial distribution of eye models provided and with the data that is already known. The product of the probability or probability density of the data with given parameters of the eye model with the probability or probability density of the parameters of the eye model is used as the consistency measure.
- Calculating/optimizing/selecting an ophthalmic lens in which at least one parameter of the individual eye model is used.

The initial distribution of the parameters of eye models provided in the first step can be in a parameterized form, e.g. (possibly multivariate) normal distribution, other distribution of the exponential family, Cauchy distribution, Dirichlet process, etc., or as a set of samples, i.e. one or more (possibly multidimensional) data sets. If the initial distribution of the parameters of eye models is parameterized, the parameters of this distribution are called "hyperparameters".

The third step (i.e. determining the parameters of an individual eye model) can include determining a multivariate probability distribution that includes both the parameters of the individual eye model and the hyperparameters of the initial distribution of the parameters of the eye model. In order to calculate the distribution of the parameters of the individual eye model from this, the distribution must be marginalized, i.e. it is integrated via the hyperparameters. The integrals can be solved with common numerical methods (e.g. using Markov Chain Monte Carlo or Hybrid Monte Carlo) and/or analytical methods. The probability or the probability density of the parameters of the eye model can in this case be calculated using the following equation:

$$\text{prob}(\vartheta_i|d_i,I) \propto \text{prob}(d_i|\vartheta_i,I) \int d\lambda \text{prob}(\vartheta_i,\lambda|I) = \text{prob}(d_i|\vartheta_i,I) \int d\lambda \text{prob}(\vartheta_i|\lambda,I) \text{prob}(\lambda|I)$$

Here prob($\vartheta_i|\lambda$,I) denotes the probability or probability density to find the parameters of the individual eye model $\vartheta_i$ in the population characterized by the hyperparameters $\lambda$. The integrals are to be carried out over the entire definition ranges of all hyperparameters $\lambda$.

Bayes B Method

As an alternative or in addition to the Bayes A method, one or more of the following steps can be carried out:
- Providing the distribution of at least one parameter of an individual eye model;
- Calculating the probability distribution of the parameters of virtual ophthalmic lenses or calculating an ensemble of ophthalmic lenses by optimizing/calculating/selecting virtual ophthalmic lenses using at least one parameter of the individual eye model;
- Manufacturing an ophthalmic lens, with the aim that the manufactured parameters of the ophthalmic lens achieve the parameters of the virtual ophthalmic lens with the highest probability.

In the first step, the distribution calculated analogously to steps 1 to 3 of the Bayes A method can be provided. In the second step, the most likely parameters $L_i$ of the ophthalmic lens are determined, i.e. on the basis of the probability distribution or probability density $$\text{prob}(L_i \mid d_i, I) = \int d\vartheta_i \text{prob}(\vartheta_i, L_i \mid d_i, I) =$$
$$\int d\vartheta_i \text{prob}(L_i \mid \vartheta_i, I) \text{prob}(\vartheta_i \mid d_i, I)$$
$$= \int d\vartheta_i \delta(L_i - L(\vartheta_i)) \text{prob}(\vartheta_i \mid d_i, I)$$

the parameters of the ophthalmic lens $L_i^{max}$ are determined, which maximize prob($L_i|d_1$,I). Here, $L_i$ initially denotes the parameters of any ophthalmic lens, and in the case of $L_i=L(\vartheta_i)$ the parameters of the ophthalmic lens created when an ophthalmic lens is optimized with the aid of an individual eye model with the parameters $\vartheta_i$. The Dirac delta distribution is denoted by $\delta(.)$.

The parameters of the ophthalmic lens can be e.g. vertex depth, refractive power at a reference point of the ophthalmic lens, refractive power distribution over an area of the ophthalmic lens, refractive errors at a reference point of the ophthalmic lens, or the distribution of the refractive errors over an area of the ophthalmic lens.

It is important that the function $L(\vartheta_1)$ can be non-linear, and therefore the maximum of the probability density prob $(\vartheta_i|d_i,I)$ (with respect to $\vartheta_i$ with $L(\vartheta_i)$ is not necessarily mapped to the maximum of the probability density prob $(L_i|d_i,I)$.

If the function $L(\vartheta_i)$ can be inverted piece by piece, the equation described above can also be solved with the help of partial integration. Other methods are also possible, e.g. numerical methods such as Particle Filter, Markov Chain Monte Carlo, or methods of parametric inference, with which a distribution of the parameters of the ophthalmic lens $L_i$ can be calculated.

Both in the Bayes A method and in the Bayes B method, independent of both the number and type of variables known by measurement (i.e. the data $d_i$ and the form of the likelihood prob$(d_1|\vartheta_i,I)$) as well as the number and type of parameters of the eye model $\vartheta_i$, there always results a consistent eye model (Bayes A and B method) and possibly a choice of the parameters of the ophthalmic lens (Bayes B method) that matches the ensemble of possible consistent eye models.

Examples Based on Probability Considerations to Solve Inconsistencies

Background to the Maximum Likelihood Approach
Basic Procedure

The initial situation is that N parameters $x_i$, $1 \leq i \leq N$ of a model are to undergo assignment and that the following information is available:
- Mean values $\mu_i$, standard deviations $\sigma_i$, and correlation coefficients $\rho_{ij}$ (with $1 \leq i, j \leq N$) of these N parameters in the population;
- Either there are no measurement values (k=0), or there are measurement values $x_i^{mess}$, $1 \leq i \leq k$ for k of these parameters (where $1 \leq k \leq N$). The probability distribution for the measurement value $x_i^{mess}$ of each parameter $x_i$ is described by a random variable $X_i$. A reliability measure is preferably available for each measurement value, e.g. a standard deviation $\sigma_i^{mess}$ of the random variable $X_i$, $1 \leq i \leq k$
- For q=N−k of these parameters there are no measurement values.
- Overall, only K of the N parameters are independent since the model requires consistency conditions that can be expressed by Q=N−K constraints.

Examples can be:
Example without HOA
  Parameters (N=15): cornea (SZA), lens front surface (SZA), lens back surface (SZA), vision disorder (SZA), eye length, lens thickness, anterior chamber depth;
  Measurement data (k=13): cornea (SZA), lens front surface (SZA), lens back surface (SZA), vision disorder (SZA), anterior chamber depth;
  Constraints (Q=3): vision disorder (SZA)=theoretical vision disorder (SZA) (calculated from the eye model assigned);
Example with HOA (up to radial order n=6)
  Parameters (N=103): cornea (SZA+HOA), lens front surface (SZA+HOA), lens back surface (SZA+HOA), vision disorder (SZA+HOA), eye length, lens thickness, anterior chamber depth;
  Measurement data (k=101): cornea (SZA+HOA), lens front surface (SZA+HOA), lens back surface (SZA+HOA), vision disorder (SZA+HOA), anterior chamber depth;
  Constraints (Q=25): vision disorder (SZA+HOA)= theoretical vision disorder (SZA+HOA) (calculated from the eye model assigned).

The basic problem to be solved is that in the case of measurement values that deviate from the population mean, a decision must be made as to whether the measurement must be discarded (e.g. if it is implausible) or must be adopted. If all measurement values are plausible in themselves, but violate one of the consistency conditions, then they must not all be adopted. Instead, a balance between the various measurement values must then be sought: those that have a very high measurement reliability should at least almost be retained, while uncertain measurement values are more likely to be adapted. Preferably, the best possible values for all N parameters are identified from the known information.

The inventive idea is based in particular on the assumption that the parameters have certain (unknown but initially fixed) values. Under this assumption, in the light of the above-mentioned information (statistical variables from the population, reliability measures of the measurements), the conditional probability density $$P^{bed}(X_1, \ldots, X_N | x_1, \ldots, x_N) \tag{1}$$

is established for the outcome of the measurements, where $X_1, \ldots, X_N$ are the random variables that vary for fixed given true values $x_1, \ldots, x_N$. Subsequently, the probability for the observed measurement values $P^{par}$ is then quantified by evaluating the function $P^{bed}$ for the k measurement values and marginalizing it for the remaining q=N−k (non-measured) parameters:

$$P^{par}(x_1, \ldots, x_N) := \int P^{bed}(X_1 = x_1^{mess}, \ldots, X_k = x_k^{mess}, X_{k+1}, \ldots, X_N | x_1, \ldots, x_N) \, dk_{k+1} \ldots dX_N \tag{2}$$

This probability density is understood as a function $P^{par}(x_1, \ldots, X_N)$ of the assumed N parameters $x_1, \ldots, x_N$. Those N parameter values for which this function assumes a maximum are then preferably considered to be the best possible values (maximum likelihood approach):

$$\frac{\partial P^{par}(x_1, \ldots, x_N)}{\partial x_i} = 0, \ 1 \leq i \leq N \tag{3}$$

As an alternative to the marginalization in Eq. (2), the N parameter values can also be defined by setting the last parameters equal to the mean values of the population, $$x_i = \mu_i, \ k+1 \leq i \leq N \tag{4}$$

while the first k parameters $x_1, \ldots, x_k$ are determined such that their expected values are equal to the measurement values:

$$\langle X_j | x_1, \ldots, x_k, x_{k+1} = \mu_{k+1}, \ldots, x_N = \mu_N \rangle = x_j^{mess} \tag{5}$$

As a further alternative, instead of the maximum formation according to equation (3) or the expected value formation according to equation (5), the medians can be used as a criterion as well.

As a further alternative, the maximum formation according to equation (3) and the expected value formation according to equation (5) as well as the median determination can also be combined as desired in order to determine the N parameter values.

Background to the Maximum Posterior Approach

The prior knowledge about the population is described by the distribution $P^{pop}(x_1, \ldots, x_N)$, which can correspond to the prior of the Bayesian description. The total probability density, which describes both the distribution of measurement values and of model parameters, is thus given by the distribution function $$P^{ges}(X_1, \ldots, X_k, x_1, \ldots, x_N) = P^{mess}(X_1, \ldots, X_k | x_1, \ldots, x_N) \times P^{pop}(x_1, \ldots, x_N) \tag{6}$$

which can correspond to the posterior of the Bayesian description except for one constant. This is why this approach is also referred to as maximum posterior.

Preferably, $P^{pop}$ is described by the multivariate normal distribution $$P^{pop}(x) = \sqrt{\frac{\det(C^{-1})}{(2\pi)^N}} \operatorname{Exp}\left(-\frac{1}{2}(x-\mu)^T C^{-1}(x-\mu)\right) \tag{7}$$

where $\mu$ is the vector of the mean values and $C$ is the covariance matrix:

$$\mu = \begin{pmatrix} \mu_1 \\ \mu_2 \\ \vdots \\ \mu_n \end{pmatrix}, C = \begin{pmatrix} \sigma_1^2 & \rho_{12}\sigma_1\sigma_2 & \cdots & \rho_{1n}\sigma_1\sigma_n \\ \rho_{12}\sigma_1\sigma_2 & \sigma_2^2 & & \rho_{2n}\sigma_2\sigma_n \\ \vdots & & \ddots & \vdots \\ \rho_{1n}\sigma_1\sigma_n & \rho_{2n}\sigma_2\sigma_n & \cdots & \sigma_n^2 \end{pmatrix} \tag{7a}$$

The measurement is described by the distribution $P^{mess}(X_1, \ldots, X_k | x_1, \ldots, x_N)$. Preferably, the measurements are independent $$P^{mess}(X_1, \ldots, X_k | x_1, \ldots, x_N) = P_1^{mess}(X_1 | x_1) \cdots P_k^{mess}(X_k | x_k) \tag{8}$$

The entire distribution function $P^{ges}$ (except for the posterior prefactor) is then given by $$P^{ges}(X_1, \ldots, X_k; x_1, \ldots, x_N) = P_1^{mess}(X_1 | x_k) \cdots P_k^{mess}(X_k | x_k) \times P^{pop}(x_1, \ldots, x_N) \tag{8a}$$

Particularly preferably, each of the measurements is normally distributed with expected value $x_i$ and standard deviation $\sigma_i^{mess}$ $$P_i^{mess}(X_i | x_i) = \frac{1}{\sqrt{2\pi}\,\sigma_i^{mess}} \operatorname{Exp}\left(-\frac{1}{2(\sigma_i^{mess})^2}(X_i - x_i)^2\right) \tag{8b}$$

The entire distribution function $P^{ges}$ is then given by inserting the normal distribution from Eq. (8b) into Eq. (8a).

It is the inventive idea to maximize $P^{ges}$ as a function of the parameters $x_1, \ldots x_N$. In order to apply the maximum posterior criterion, it is preferred to form the derivatives of the logarithm $$\frac{\partial}{\partial x_i} \log P^{ges}(X_1, \ldots, X_k, x_1, \ldots, x_N) = \tag{9}$$

$$\frac{\partial}{\partial x_i} [\log P^{mess}(X_1, \ldots, X_k | x_1, \ldots, x_N) + \log P^{pop}(x_1, \ldots, x_N)] =$$

$$\frac{\partial P^{mess}(X_1, \ldots, X_k | x_1, \ldots, x_N)/\partial x_i}{P^{mess}(X_1, \ldots, X_k | x_1, \ldots, x_N)} + \frac{\partial P^{pop}(x_1, \ldots, x_N)}{P^{pop}(x_1, \ldots, x_N)}, 1 \leq i \leq N$$

$$\frac{\partial}{\partial x_i} \log P^{ges}(X_1, \ldots, X_k, x_1, \ldots, x_N) = \frac{\partial}{\partial x_i} [\log P_1^{mess}(X_1 | x_1) + \ldots + \tag{10}$$

$$\log P_k^{mess}(X_k | x_k) + \log P^{pop}(x_1, \ldots, x_N)] = \frac{\partial P_i^{mess}(X_i | x_i)/\partial x_i}{P_i^{mess}(X_i | x_i)} +$$

$$\frac{\partial P^{pop}(x_1, \ldots, x_N)}{P^{pop}(x_1, \ldots, x_N)}, 1 \leq i \leq N$$

If the distributions are multivariate normally distributed, as is particularly preferred, equation (9) or equation (10) represents a linear system of equations with N equations and N variables that can be solved for $x_1, \ldots, x_N$.

a) No Constraints

If there are no constraints and equation (9) can be solved, then unique solutions for $x_1, \ldots, x_N$ result. If the distributions are multivariate normally distributed, as is particularly preferred, and if the measurement uncertainties are significantly smaller than the ranges of variation of the population, $\sigma_i^{mess} \ll \sigma_i$, $1 \leq i \leq k$, then the solutions result $$x_i \approx x_i^{mess}, \quad 1 \leq i \leq k \tag{11}$$

$$x_i \approx \mu_i + \Delta x_i, \quad k+1 \leq i \leq N$$

i.e. for all parameters for which measurement values are available, one essentially believes the measurement values, and for the remaining values one obtains the mean values $\mu_i$ of the population plus shifts $\Delta x_i$ due to the correlations with the measurement values. One embodiment of the invention then consists in adopting the measurement values for $1 \leq i \leq k$ directly and neglecting their slight shift due to the underlying population.

b) Constraints

If there are constraints between the parameters, then every member of the population also satisfies these constraints. Constraints can be described by $$f_j(x_1, \ldots, x_N) = 0, \quad 1 \leq j \leq Q \Leftrightarrow f(x_1, \ldots, x_N) = 0 \tag{12}$$

i.e. by Q functions $f_j$ of the parameters $x_1, \ldots, x_N$, which can be combined in a vector $f$ and which, by requirement, are to be equal to zero. The functions $f_j$ are preferably linear or linear approximations to the given constraints.

In the preferred case of multivariate distributions, this has the consequence that the columns of the covariance matrix are linearly dependent, that is to say that the covariance matrix has a rank $r<N$ and can therefore no longer be inverted. A distribution density $P^{pop}(x_1, \ldots, x_N)$ can then no longer be specified.

One possibility in practice is to regularize the covariance matrix $C$ by shifting one or more of the correlations $\rho_{ij}$ or standard deviations $\sigma_i$ contained in it by $\varepsilon$ and then determining $x_1, \ldots, x_N$. The solutions thus obtained then automatically satisfy the constraints for $\varepsilon \to 0$.

In the context of the invention, it has been found that this method has disadvantages though. On the one hand, one has to know the distribution in the population, and on the other hand, its covariance matrix is either singular or poorly conditioned. If one researches the correlations $\rho_{ij}$ and standard deviations $\sigma_i$, then small inaccuracies in the information or incomplete information are sufficient for the covariance matrix to be regular, but then possibly generate numerically unstable solutions for the parameters sought.

In the context of the invention, however, it has been found that this problem can be circumvented by either working on the basis of the distribution (maximum likelihood approach)

$$P^{mess}(x_1, \ldots, x_N) := P^{mess}(X_1 = x_1^{mess}, \ldots, X_k = x_k^{mess} | x_1, \ldots, x_N) \quad (13a)$$

or on the basis of the distribution (maximum posterior approach)

$$P^{ges}(x_1, \ldots, x_N) := P^{ges}(X_1 = x_1^{mess}, \ldots, X_k = x_k^{mess}; x_1, \ldots, x_N) \quad (13b)$$

The substitution method can preferably be used for this purpose.

Maximum Likelihood Method with Constraints and Substitution

The first K parameters $x^u := (x_1, \ldots, x_K)^T$ are assumed to be independent and equation (12) is solved for the remaining $Q = N - K$ dependent parameters $x^a := (x_{K+1}, \ldots, x_N)^T$, which can then be understood as a function $x^a(x^u)$ of the independent parameters $x^u$ and can be substituted in f. Then the constraints as a function of $x^u$ are:

$$f(x^u, x^a(x^u)) = 0 \quad (14).$$

In the context of the invention, it is not necessary to explicitly know the function $x^a(x^u)$. In the context of the invention, one only needs its Jacobi matrix $\partial x^a / \partial x^u := \partial x_i^a / \partial x_j^u$, $1 \le i \le Q$, $1 \le j \le K$, which according to the theorem of the implicit function is given by $$\frac{\partial x^a}{\partial x^u} = -\left(\frac{\partial f}{\partial x^a}\right)^{-1} \frac{\partial f}{\partial x^u} \quad (15)$$

where $\partial f / \partial x^a$ is the quadratic Jacobi matrix of f with regard to $x^a$ and $\partial f / \partial x^u$ is the generally rectangular Jacobi matrix of f with regard to $x^u$. The probability density $P^{mess}(x^u, x^a(x^u))$ thus has to be maximized as a function of $x^u$, i.e.

$$\frac{\partial}{\partial x^u} P^{mess}(x^u, x^a(x^u)) = \frac{\partial P^{mess}}{\partial x^u} + \frac{\partial P^{mess}}{\partial x^a} \frac{\partial x^a}{\partial x^u} \quad (16)$$
$$= \frac{\partial P^{mess}}{\partial x^u} - \frac{\partial P^{mess}}{\partial x^a}\left(\frac{\partial f}{\partial x^a}\right)^{-1} \frac{\partial f}{\partial x^u}$$
$$= 0$$

The system of equations (16) is K equations that can be solved for the parameters $x^u$ independent for K. The remaining parameters $x^a$ are obtained by inserting them into the context $x^a(x^u)$.

Maximum Likelihood Method with Constraints and Lagrange Parameters

Alternatively, within the scope of the invention, the entire set of parameters can be considered independent if, instead of the function $P^{mess}(x_1, \ldots, x_N)$, the Lagrange function is maximized $$P^{mess,Lagrange}(x_1, \ldots, x_N, \lambda) = P^{mess}(x_1, \ldots, x_N) + \lambda f(x_1, \ldots, x_N) \quad (17)$$

where $\lambda = (\lambda_1, \ldots, \lambda_Q)$ is a Q-dimensional vector of Lagrange multipliers. It is then to be maximized by setting the derivatives N+Q to zero $$\frac{\partial}{\partial x_i} P^{mess,Lagrange}(x_1, \ldots, x_N, \lambda) = 0, \quad 1 \le i \le N \quad (18)$$

$$\frac{\partial}{\partial \lambda_j} P^{mess,Lagrange}(x_1, \ldots, x_N, \lambda) = 0, \quad 1 \le j \le Q.$$

Solving equation (18) for the N+Q unknowns $(x_1, \ldots, x_N)$ and $(\lambda_1, \ldots, \lambda_Q)$ leads to the solutions for the parameters.

Instead of treating the constraints with substitution or long-range parameters, one can alternatively (for example in the case of locally vanishing gradients of the function to be maximized) use a damped Hamilton formalism with a friction term.

Analogously, the method of Eqs. (16) to (18) can be applied to the function $P^{ges}(x_1, \ldots, x_N)$ instead of $P^{mess}(x_1, \ldots, x_N)$ and then represents a maximum-posterior method with constraints.

Embodiment with Specific Exemplary Numerical Values

For the sake of simplicity, an eye that is rotationally symmetrical about the optical axis and therefore has neither a cylindrical prescription, nor a cylindrical cornea, nor cylindrical lens surfaces is considered as a starting situation. Exemplary values and parameters prior to the IOL surgery are in detail:

$S = -7.0$ dpt; vision disorder (measured)

$C = 41.2$ dpt; refractive power of cornea (measured)

$L_1 = 7.82$ dpt; refractive power of lens front surface (literature)

$L_2 = 13.28$ dpt; refractive power of lens back surface (literature)

$d_{CL} = 3.6$ mm; anterior chamber depth (measured)

$d_L = 3.7$ mm; lens thickness (literature)

$n_{CL} = 1.336$; refractive index anterior chamber (literature)

$n_L = 1.422$; refractive index lens (literature)

$n_{LR} = 1.336$; refractive index vitreous body (literature) $\quad (19)$.

After IOL surgery, for example the following values or parameters are transmitted:

$S_{IOL}^{mess} = 0.0$ dpt; vision disorder (measured)

$L_{2,IOL}^{mess} = 3.2$ dpt; refractive power of lens back surface (manufacturer information) $\quad (20)$.

All other parameters after IOL surgery are assumed to be unchanged for the sake of simplicity.

With the aid or equation $$D_{LR} = L_2 + \left(L_1 + \frac{S+C}{1-\tau_{CL}(S+C)}\right)\left(1 - \tau_L\left(L_1 + \frac{S+C}{1-\tau_{CL}(S+C)}\right)\right)^{-1} \quad (21)$$

one can calculate the reduced inverse vitreous length ($D_{LR} = n_{LR}/d_{LR}$, where $d_{LR}$ the vitreous length is; further $\tau_{CL} = d_{CL}/n_{CL}$ and $\tau_L = d_{CLL}/n_L$), and thus the eye length $d_A = d_{CL} + d_L + d_{LR}$. Vitreous body length and eye length are so directly related that in the following the vitreous body length can be considered instead of the eye length.

If one applies equation (21) to the situations before and after surgery, one formally obtains prior to IOL surgery $$D_{LR} = 64.69 \text{ dpt} \tag{22a}$$

and formally after IOL surgery $$D_{LR,IOL}^{mess} = 65.65 \text{ dpt} \tag{22b}.$$

However, since the vitreous body length cannot have changed as a result of surgery, there is an inconsistency here that can be solved within the scope of the present invention.

In order to choose the simplest possible example, the initial situation can be regarded as the case that there are no variations and no correlations in the basic population, and that only the vision disorder measured afterward as well as the IOL itself are subject to uncertainties:

$\sigma_{S,IOL}^{mess} = 0.25$ dpt; vision disorder (Std. deviation of measurement method)

$\sigma_{L2,IOL}^{mess} = 0.4$ dpt; refractive power of lens back surface (manufacturer tolerance) (23).

Now, within the scope of the invention, the true values of $S_{IOL}, L_{2,IOL}$ can be identified which, as expected, will both deviate from equation (20).

In the exemplary case, $P^{pop} = 1$ and the probability density for the distribution of $S_{IOL}, L_{2,IOL}$ to be initially assumed based on the measurements is $$P^{mess}(S_{IOL}^{mess}, L_{2,IOL}^{mess} \mid S_{IOL}, L_{2,IOL}) = \tag{24}$$

$$P_1^{mess}(S_{IOL}^{mess} \mid S_{IOL}) \ldots P_k^{mess}(L_{2,IOL}^{mess} \mid L_{2,IOL}) =$$

$$\frac{1}{2\pi\sigma_{S,IOL}^{mess}\sigma_{L2,IOL}^{mess}} \times$$

$$\text{Exp}\left(-\frac{1}{2(\sigma_{s,IOL}^{mess})^2}(S_{IOL} - S_{IOL}^{mess})^2\right) \times$$

$$\text{Exp}\left(-\frac{1}{2(\sigma_{L2,IOL}^{mess})^2}(L_{2,IOL} - L_{2,IOL}^{mess})^2\right).$$

Now, however, the constraint applies that $S_{IOL}, L_{2,IOL}$ after insertion in equation (21) have to yield the same value for $D_{LR}$ after surgery as before surgery. Hence the equation for the constraint is $$D_{LR} = \tag{25}$$

$$L_{2,IOL} + \left(L_1 + \frac{S_{IOL} + C}{1 - \tau_{CL}(S_{IOL} + C)}\right)\left(1 - \tau_L\left(L_1 + \frac{S_{IOL} + C}{1 - \tau_{CL}(S_{IOL} + C)}\right)\right)^{-1}$$

which when solved for $L_{2,IOL}$ yields as a function of $S_{IOL}$:

$$L_{2,IOL}(S_{IOL}) = \tag{26}$$

$$D_{LR} - \left(L_1 + \frac{S_{IOL} + C}{1 - \tau_{CL}(S_{IOL} + C)}\right)\left(1 - \tau_L\left(L_1 + \frac{S_{IOL} + C}{1 - \tau_{CL}(S_{IOL} + C)}\right)\right)^{-1}.$$

Figure 2:
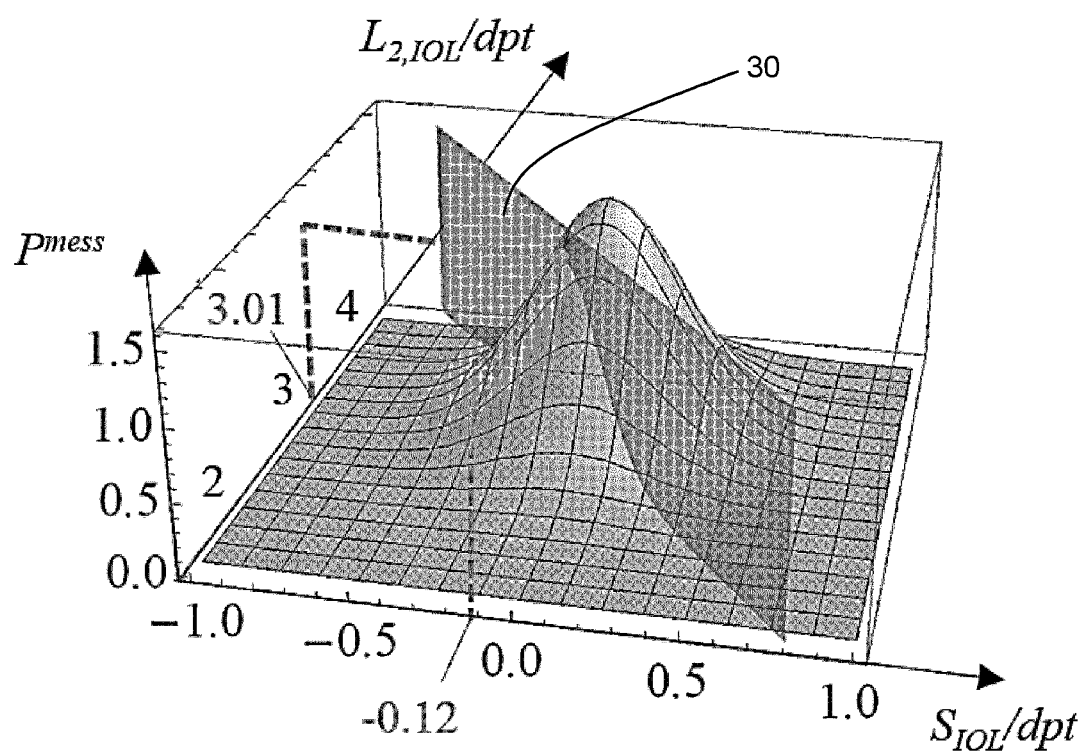
FIG. 2 a graph with an exemplary dependency of $P^{mess}$ on $S_{IOL}$ and $L_{2,IOL}$ to illustrate and explain a method for determining parameters under constraint conditions according to a preferred embodiment of the present invention.

The constraint means that one may only move on the cutting surface 30 shown in FIG. 2.

If one substitutes $L_{2,IOL}(S_{IOL})$ in equation (24) and maximizes for $S_{IOL}$, i.e. if one solves $$\frac{d}{dS_{IOL}} P^{mess}(S_{IOL}^{mess}, L_{2,IOL}^{mess} \mid S_{IOL}, L_{2,IOL}(S_{IOL})) = 0 \tag{27}$$

for $S_{IOL}$, one obtains $S_{IOL} = -0.12$ dpt $L_{2,IOL}(S_{IOL}) = 3.01$ dpt (28).

Both variables $S_{IOL}, L_{2,IOL}$ are therefore in the negative direction compared to the measurement values, but not to the same extent. Rather, the method seeks a balance in the light of the different standard deviations and the asymmetrical position of the constraint relative to the Gaussian bell.

Inconsistencies in the eye model can occur not only for a calculated eye length (or a calculated lens-retina distance), but also e.g. when measuring the eye length. Such inconsistencies can be solved analogously to the example of a calculated eye length described above. Of course, more complex examples in which the eye length itself is also not fixed or where possibly correlations occur, can also be given.

REFERENCE NUMERAL LIST

10 main ray
12 eye
14 first surface of the spectacle lens (front surface)
16 second surface of the spectacle lens (back surface)
18 corneal front surface
20 eye lens
30 cutting surface

The invention claimed is:

1. A computer-implemented method for identifying relevant individual parameters of at least one eye of a spectacle wearer for the calculation or optimization of a spectacle lens for the at least one eye of the spectacle wearer, wherein an intraocular lens was implanted in the at least one eye of the spectacle wearer as part of surgery, comprising:
   providing individual refraction data on the at least one eye of the spectacle wearer;
   defining an individual eye model in which at least:
      a shape and/or power of a corneal front surface of a model eye;
      a cornea-lens distance;
      parameters of the lens of the model eye; and
      a lens-retina distance
   are defined as parameters of the individual eye model, wherein defining the parameters of the individual eye model takes place on the basis of data on visual acuity correction of the at least one eye having the intraocular lens and further on the basis of individual measurement values for the eye of the spectacle wearer and/or standard values and/or on the basis of the provided individual refraction data such that the model eye has the provided individual refraction data;
   providing an initial distribution of parameters of the eye model and individual data on properties of the at least one eye; and
   determining the parameters of the individual eye model on the basis of the initial distribution of parameters of the eye model and the individual data using probability calculations.

2. The computer-implemented method according to claim 1, wherein defining the parameters of the individual eye model takes place on the basis of intraocular lens data and further on the basis of individual measurement values for the eye of the spectacle wearer and/or standard values and/or on the basis of the provided individual refraction data such that the model eye has the provided individual refraction data, wherein defining the parameters of the lens of the model eye takes place on the basis of the intraocular lens data.

3. The computer-implemented method according to claim 1, wherein a lens-retina distance of the eye of the spectacle wearer is identified, and defining the parameters of the individual eye model takes place on the basis of the identified lens-retina distance and further on the basis of individual measurement values for the eye of the spectacle wearer and/or standard values and/or on the basis of the provided individual refraction data such that the model eye has the provided individual refraction data, wherein the lens-retina distance of the model eye is defined by the identified lens-retina distance of the eye of the spectacle wearer.

4. The computer-implemented method according to claim 1, wherein defining the lens-retina distance takes place by measuring and/or calculating.

5. The computer-implemented method according to claim 2,
wherein the intraocular lens data comprises at least a defocus of the front surface of the intraocular lens, a defocus of the back surface of the intraocular lens, and a thickness of the intraocular lens; and/or
wherein the intraocular lens data comprises at least a defocus of the refractive power of the intraocular lens, and/or
wherein the intraocular lens data includes a specification of the A constant.

6. The computer-implemented method according to claim 2, wherein the intraocular lens data is provided on the basis of type or serial number information.

7. The computer-implemented method according to claim 1, further comprising:
carrying out a consistency check of the defined eye model, and
solving any inconsistencies with the aid of analytical and/or numerical and/or probabilistic methods.

8. The computer-implemented method according to claim 7, wherein any inconsistencies are solved by:
adapting one or more parameters of the eye model, wherein several parameters of the eye model are adapted and the adaptation is divided among the several parameters of the eye model;
and/or adding at least one new parameter to the eye model and defining it such that the eye model becomes consistent; and/or
adapting a target power of the ophthalmic lens.

9. The computer-implemented method according to claim 1, wherein the parameters of the eye model are determined with the aid of probabilistic methods using Bayesian statistics and/or a maximum likelihood algorithm.

10. The computer-implemented method according to claim 1, wherein the provided individual refraction data on the at least one eye of the spectacle wearer is individual post-surgery refraction data of the at least one eye of the spectacle wearer, and wherein the individual eye model is a post-surgery eye model.

11. The computer-implemented method according to claim 10, further comprising:
providing individual pre-surgery refraction data of the at least one eye of the spectacle wearer,
wherein determining a lens-retina distance of the eye of the spectacle wearer is based on an individual pre-surgery eye model using the provided individual pre-surgery refraction data.

12. The computer-implemented method according to claim 11, wherein in the pre-surgery eye model at least:
a shape and/or power of a corneal front surface of a model eye of the pre-surgery eye model;
a cornea-lens distance of the model eye of the pre-surgery eye model;
parameters of the lens of the model eye of the pre-surgery eye model; and
a lens-retina distance of the model eye of the pre-surgery eye model are defined on the basis of individual measurement values for the eye of the spectacle wearer and/or standard values and/or on the basis of the provided individual pre-surgery refraction data such that the model eye has the provided individual pre-surgery refraction data, wherein at least defining the lens-retina distance takes place by measuring and/or calculating.

13. A computer-implemented method for calculating or optimizing a spectacle lens for at least one eye of a spectacle wearer, comprising:
a method for identifying relevant individual parameters of the at least one eye of the spectacle wearer according to claim 1;
specifying a first surface and a second surface for the spectacle lens to be calculated or optimized;
identifying the course of a main ray through at least one visual point of at least one surface of the spectacle lens to be calculated or optimized into the model eye;
evaluating an aberration of a wavefront resulting from a spherical wavefront incident on the first surface of the spectacle lens along the main ray on an evaluation surface compared to a wavefront converging in one point on the retina of the eye model; and
iteratively varying the at least one surface of the spectacle lens to be calculated or optimized until the evaluated aberration corresponds to a predetermined target aberration.

14. A method for producing a spectacle lens, comprising:
calculating or optimizing a spectacle lens according to the method for calculating or optimizing a spectacle lens according to claim 13; and
manufacturing the thus-calculated or optimized spectacle lens.

15. A device for identifying relevant individual parameters of at least one eye of a spectacle wearer for the calculation or optimization of a spectacle lens for the at least one eye of the spectacle wearer, the at least one eye of the spectacle wearer having an implanted intraocular lens, comprising:
at least one data interface configured to provide individual refraction data on the at least one eye of the spectacle wearer; and
a modeling module configured to define an individual eye model, which at least defines
a shape and/or power of a corneal front surface of a model eye;
a cornea-lens distance;
parameters of the lens of the model eye; and
a lens-retina distance of the individual eye model, wherein defining the parameters of the individual eye model takes place on the basis of data on visual acuity correction of the at least one eye having the intraocular lens and further on the basis of individual measurement values for the eye of the spectacle wearer and/or standard values and/or on the basis of the provided individual refraction data such that the model eye has the provided individual refraction data, wherein the individual eye model is defined by providing an initial distribution of parameters of the eye model and individual data on properties of the at least one eye; and wherein the parameters of the individual eye model are determined on the basis of the initial distribution of parameters of the eye model and the individual data using probability calculations.

16. The device according to claim 15, wherein defining the parameters of the individual eye model takes place on the basis of intraocular lens data and further on the basis of individual measurement values for the eye of the spectacle wearer and/or standard values and/or on the basis of the provided individual refraction data such that the model eye has the provided individual refraction data, and wherein defining the parameters of the lens of the model eye takes place on the basis of the intraocular lens data.

17. The device according to claim 15, wherein a lens-retina distance of the eye of the spectacle wearer is identified by the modeling module and defining the parameters of the individual eye model takes place on the basis of the identified lens-retina distance and further on the basis of individual measurement values for the eye of the spectacle wearer and/or standard values and/or on the basis of the provided individual refraction data such that the model eye has the provided individual refraction data, and wherein the lens-retina distance of the model eye is defined by the identified lens-retina distance of the eye of the spectacle wearer.

18. A device for calculating or optimizing a spectacle lens for at least one eye of a spectacle wearer, comprising:
a device configured to identify relevant individual parameters of the at least one eye of the spectacle wearer according to claim 15;
a surface model database configured to specify a first surface and a second surface for the spectacle lens to be calculated or optimized;
a main ray identification module configured to identify the course of a main ray through at least one visual point of at least one surface of the spectacle lens to be calculated or optimized into the model eye;
an evaluation module configured to evaluate an aberration of a wavefront resulting from a spherical wavefront incident on the first surface of the spectacle lens along the main ray on an evaluation surface compared to a wavefront converging in one point on the retina of the eye model; and
an optimization module configured to iteratively vary the at least one surface of the spectacle lens to be calculated or optimized until the evaluated aberration corresponds to a predetermined target aberration.

19. A device for producing an ophthalmic lens, comprising:
a calculator or optimizer configured to calculate or optimize the spectacle lens according to a method for calculating or optimizing a spectacle lens according to claim 13; and
a machining configured to machine the spectacle lens in accordance with the result of the calculation or optimization.

20. A non-transitory computer program product including program code configured to, when loaded and executed on a computer, perform a method for identifying relevant individual parameters of at least one eye of a spectacle wearer according to claim 1.

21. A non-transitory computer program product including program code configured to, when loaded and executed on a computer, perform a method for calculating or optimizing a spectacle lens according to claim 13.

22. A spectacle lens produced by a method according to claim 14.

* * * * *